(12) United States Patent
Dakka et al.

(10) Patent No.: US 8,604,110 B2
(45) Date of Patent: Dec. 10, 2013

(54) ALKYL AROMATIC PLASTICIZERS AND METHODS OF MAKING

(75) Inventors: Jihad Mohammed Dakka, Whitehouse Station, NJ (US); Stephen Zushma, Clinton, NJ (US); Christine A. Costello, Easton, PA (US); Edmund John Mozeleski, Califon, NJ (US); Diana S. Smirnova, High Bridge, NJ (US); Allen David Godwin, Seabrook, TX (US); Pierre J. Osterrieth, Brussels (BE); Jörg Friedrich Wilhelm Weber, Houston, TX (US); Paul Hamden Daniels, League City, TX (US); Thomas M. Larson, Bellaire, TX (US); Catherine A. Faler, Houston, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 168 days.

(21) Appl. No.: 13/198,851

(22) Filed: Aug. 5, 2011

(65) Prior Publication Data

US 2013/0035431 A1 Feb. 7, 2013

(51) Int. Cl.
*C08K 5/12* (2006.01)
*C07C 69/75* (2006.01)

(52) U.S. Cl.
USPC .......................................................... 524/287

(58) Field of Classification Search
USPC ........................................ 560/81, 82; 524/287
See application file for complete search history.

(56) References Cited

U.S. PATENT DOCUMENTS

| | | | |
|---|---|---|---|
| 1,848,155 A | 3/1932 | Boehmer | |
| 2,520,084 A | 8/1950 | Dazzi | |
| 3,010,990 A * | 11/1961 | Kerschner et al. | 560/124 |
| 4,294,976 A | 10/1981 | Itatani et al. | |
| 6,274,756 B1 | 8/2001 | Caers et al. | |
| 6,482,972 B1 | 11/2002 | Bahrmann et al. | |
| 6,740,254 B2 | 5/2004 | Zhou et al. | |
| 6,777,514 B2 | 8/2004 | Patil et al. | |
| 7,297,738 B2 | 11/2007 | Gosse et al. | |
| 7,579,511 B1 | 8/2009 | Dakka et al. | |
| 2006/0247461 A1 | 11/2006 | Schlosberg et al. | |
| 2008/0242895 A1 | 10/2008 | Godwin et al. | |
| 2010/0159177 A1 | 6/2010 | Dakka et al. | |

OTHER PUBLICATIONS

E.J. Hennessey and S.L. Buchwald, "A General and Mild Copper-Catalyzed Arylation of Diethyl Malonate", Org. Lett., vol. 4, 2002, pp. 269-272.

A. Mukhopadhyay, G. Rothenberg, D. Gitis and Y. Sasson, "Tandem One-Pot Palladium-Catalyzed Reductive and Oxidative Coupling of Benzene and Chlorobenzene", J. Org. Chem, vol. 65, 2000, pp. 3107-3110.

* cited by examiner

Primary Examiner — Tae H Yoon
(74) Attorney, Agent, or Firm — Robert A. Migliorini

(57) ABSTRACT

Provided are compounds of the formula:

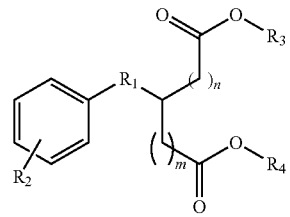

wherein m=0-3 and n=0-3, and
$R_1$ represents $C_xH_{2x}$ wherein x=0 to 4 or cyclohexane; $R_2$ represents H, a $C_1$-$C_6$ alkyl group at any of the ortho-, meta- or para-positions, a residue including heteroatoms chosen from O, N, and S, or mixtures thereof; and $R_3$ and $R_4$ represent hydrocarbon residues of OXO-$C_5$-$C_9$ alcohols which are different isomers of equal carbon number or different in carbon number. Also provided are processes for making the compounds and plasticized polymer compositions containing said compounds.

5 Claims, No Drawings

ALKYL AROMATIC PLASTICIZERS AND METHODS OF MAKING

FIELD

This disclosure is related to a potential route to non-phthalate, OXO-(di)ester plasticizers.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, U.S. Application No. 2006/0247461, and U.S. Pat. No. 7,297,738.

Other suggested substitutes include esters based on benzoic acid (see, for instance, U.S. Pat. No. 6,740,254, and also co-pending, commonly-assigned, U.S. Provisional Patent Application No. 61/040,480, filed Mar. 28, 2008 and polyketones, such as described in U.S. Pat. No. 6,777,514; and also co-pending, commonly-assigned, U.S. Patent Publication No. 2008/0242895, filed Mar. 28, 2008. Epoxidized soybean oil, which has much longer alkyl groups ($C_{16}$ to $C_{18}$) has been tried as a plasticizer, but is generally used as part of a PVC stabilizer system to protect the PVC polymer from thermally induced decomposition. Co-pending and commonly-assigned U.S. Patent Publication No. 2010/0159177 discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins.

Matsuda et al., "Synthesis and Properties of Dialkyl Esters of Benzylsuccinic Acid", Kogyo Kagaku Zasshi, vol. 58, pp. 60-62 (1955) disclose $C_1$-$C_6$, $C_8$, $C_{10}$ and lauryl esters of benzylsuccinic anhydride. The $C_4$, $C_6$ and $C_8$ esters demonstrated good plasticizing properties for polyvinyl chloride. The starting benzylsuccinic anhydride material was formed by treating 10 parts toluene with 1 part maleic anhydride in an autoclave.

JP32-000043 (1957) "Plasticizers for Polyvinyl Resins", to Matsuda discloses $C_1$-$C_8$ esters of aralkylsuccinic acids, such as benzylsuccinic acid, p-methylbenzylsuccinic acid or p-toluoylisopropylsuccinic acid. The esters are disclosed as useful for plasticizing polyvinyl resins.

Matsuda et al., "Properties of Dialkylesters of Benzyl- and Hexahydrobenzylsuccinic Acid as Plasticizers and Lubricant", Kogyo Kagaku Zasshi, vol. 60, pp. 286-288 (1957) disclose properties of dialkylesters of benzyl- and hexahydrobenzylsuccinic acid as plasticizers and lubricants. In particular, 2-ethylhexyl and n-octyl esters of benzylsuccinic acid appeared to be more promising as plasticizers for polyvinyl chloride.

Vol'chenko et al., "Plasticizing a Chloroprene Latex L-7 Polymer to Increase Frost-Resistance of Latex Products", Kauchuk i Resina; vol. 26(4), pp. 15-17 (1967) disclose didecyl benzylsuccinate as a plasticizer for chloroprene latex.

EP 13506 B to Renshaw discloses plasticizers for vinyl chloride polymers containing aromatic diesters, non-aromatic diesters and optionally hydrocarbons. The aromatic diesters can be $C_3$-$C_6$ alkyl benzyl succinates.

U.S. Pat. No. 1,848,155 to Boehmer discloses esters of secondary butyl alcohols, wherein the ester can be a secondary butyl ester of phenylsuccinic acid.

Thus what is needed is a method of making a general purpose non-phthalate plasticizer having and providing a plasticizer having suitable melting or chemical and thermal stability, pour point, glass transition, increased compatibility, good performance and low temperature properties.

SUMMARY

In one aspect, the present application is directed to compounds of the formula:

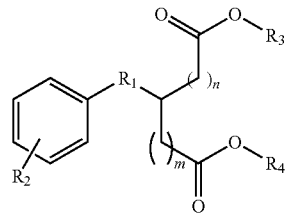

wherein m=0-3, and n=0-3, and
wherein $R_1$ represents $C_xH_{2x}$ x=0-4 or $R_1$ represents cyclohexane; $R_2$ represents H, a $C_1$-$C_6$ alkyl group at any of the ortho-, meta- or para-positions, a residue including heteroatoms chosen from O, N, and S, or mixtures thereof; and $R_3$ and $R_4$ represent hydrocarbon residues of OXO-$C_5$-$C_9$ alcohols which are different isomers of equal carbon number or different in carbon number.

Advantageously, $R_1$ may be $CH_2$, $CH_2$—$CH_2$, $CH$—$CH_3$, $CH_2$—$CH_2$—$CH_2$, $CH$—$CH_2$—$CH_3$, $CH_3$—$C$—$CH_3$, $CH_3$—$CH_2$—$C$—$CH_3$, $CH$—$CH_2$—$CH_2$—$CH_3$, or $CH_2$—$CH_2$—$CH_2$—$CH_2$.

Likewise, according to the formula, $R_2$ can be H, or ethyl, or a cyclic $C_5$ or $C_6$ hydrocarbon, such as phenyl, or tert-butyl, or iso-propyl, or even methoxy.

In a preferred embodiment of the compounds, $R_3$ and $R_4$ are hydrocarbon residues of $C_6$-$C_7$ OXO-alcohols Additionally, the compounds can be of any of the following formulae:

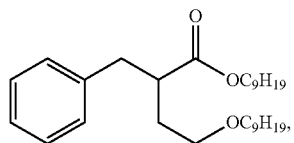
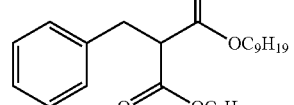
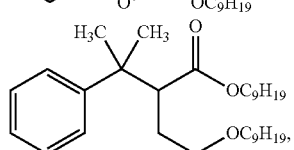
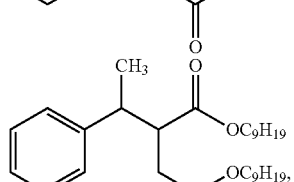
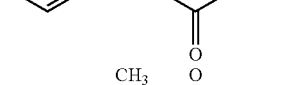
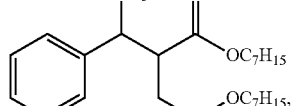
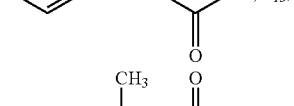
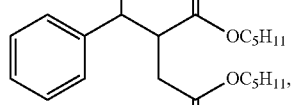
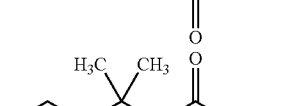
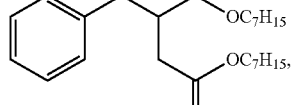
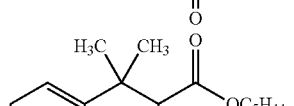
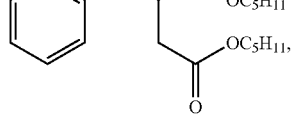

-continued

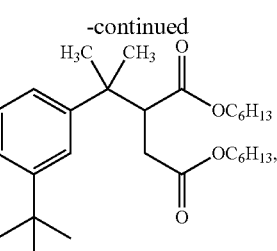
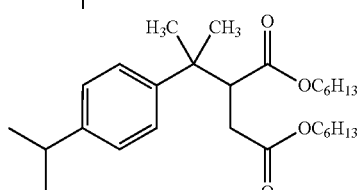
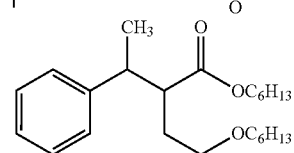
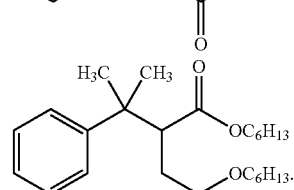
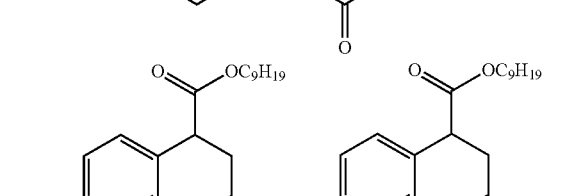
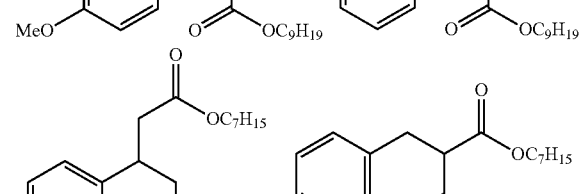
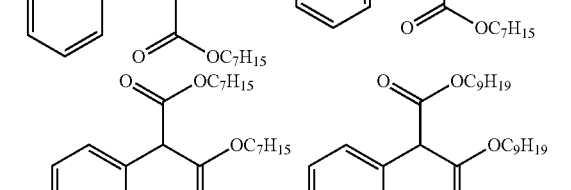
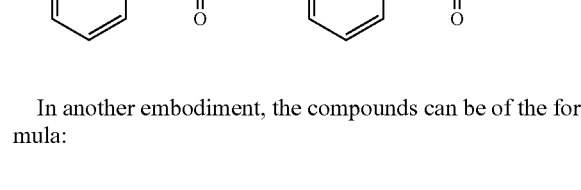

In another embodiment, the compounds can be of the formula:

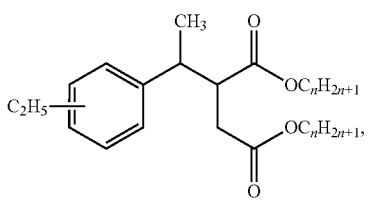

wherein the ethyl substituent (—C$_2$H$_5$) is in the ortho-, meta- or para-position, or mixtures of these isomers at different ratios, and n=6 or 7.

Another embodiment of the present disclosure is directed to a polymer composition comprising a thermoplastic polymer and at least one plasticizer comprising compounds of the formula:

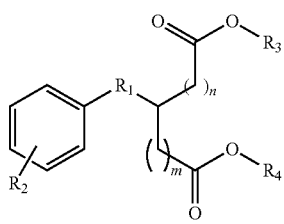

wherein m=0-3, and n=0-3, and wherein R$_1$ represents C$_x$H$_{2x}$, x=0-4 or R$_1$ represents cyclohexane; R$_2$ represents H, a C$_1$-C$_6$ alkyl group at any of the ortho-, meta- or para-positions, a residue including heteroatoms chosen from O, N, and S, or mixtures thereof; and R$_3$ and R$_4$ represent hydrocarbon residues of OXO-C$_5$-C$_9$ alcohols which are different isomers of equal carbon number or different in carbon number.

Preferably the polymer of the composition is selected from the group consisting of vinyl chloride resins, polyesters, polyurethanes, ethylene-vinyl acetate copolymer, rubbers, poly(meth)acrylics and combinations thereof, and more preferably is polyvinylchloride.

Another embodiment of the present disclosure is directed to a process for making compounds of the formula:

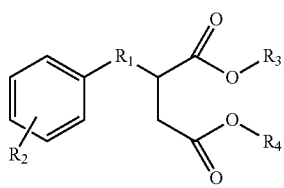

comprising:

reacting an aromatic compound of the formula

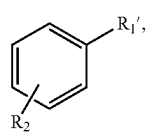

wherein R$_1$' represents C$_x$H$_{2x+1}$ x=0-4 or R$_1$ represents cyclohexane R$_2$ represents H, a C$_1$-C$_6$ alkyl group at any of the ortho-, meta- or para-positions, a residue including heteroatoms chosen from O, N, and S, or mixtures thereof, with maleic anhydride in the presence of a free radical alkylation initiator, to form compounds of the formula:

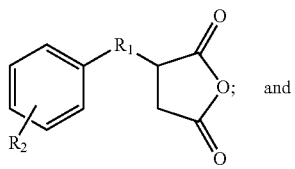

esterifying the anhydride moiety with one or more OXO-C$_5$-C$_9$ alcohols, which are different isomers of equal carbon number or different in carbon number under esterification conditions to form said compounds of formula:

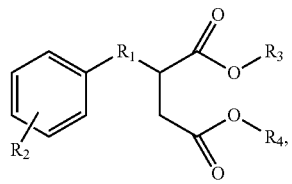

wherein R$_1$ represents C$_x$H$_{2x}$ x=0-4 or R$_1$ represents cyclohexane, R$_2$ represents H, a C$_1$-C$_6$ alkyl group at any of the ortho-, meta- or para-positions, a residue including heteroatoms chosen from O, N, and S, or mixtures thereof, R$_3$ and R$_4$ represent hydrocarbon residues of said OXO-C$_5$-C$_9$ alcohols.

Advantageously, R$_2$ can be hydrogen, phenyl, or ethyl.

In a preferred embodiment of the process, the compounds formed are a mixture isomers wherein R$_2$ is in the ortho-, meta- or para-positions.

In a particularly preferred embodiment of the process, R$_3$ and R$_4$ represent hydrocarbon residues of C$_6$ or C$_7$ OXO-alcohols.

Additionally, the free radical initiator used in the process can be air, n-hydroxyphthalimide (NHPI), azobisisobutyronitrile (AIBN), t-butylperoxide, or cumene hydroperoxide, or combinations thereof.

Another embodiment of the present disclosure is directed to a process for making compounds of the formula:

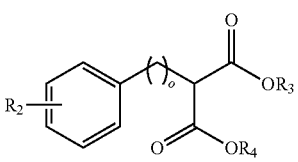

comprising reacting a compound of the formula:

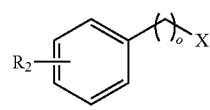

with a diester of malonic acid, wherein X is any halide, R$_2$ represents H, a C$_1$-C$_6$ alkyl group at any of the ortho-, meta- or para-positions, a residue including heteroatoms chosen from O, N, and S, or mixtures thereof, R$_3$ and R$_4$ represent hydrocarbon residues of said OXO-C$_5$-C$_9$ alcohols, and o=0 or 1.

DETAILED DESCRIPTION

There is an increased interest in developing new plasticizers that are non-phthalates and which possess good plasticizer performance characteristics but are still competitive economically. The present disclosure is directed towards non-phthalate, OXO-(di)ester plasticizers that can be made from low cost feeds and employ fewer manufacturing steps in order to meet economic targets.

According to the present disclosure, non-phthalate plasticizers are produced from an aromatic anhydride, made from aromatic compounds or hydrocarbyl-substituted aromatic compounds, by alkylation with free radicals formed from an unsaturated cyclic anhydride, which anhydride moiety is then esterified with OXO $C_4$-$C_{13}$ alcohols (ROH). One non-limiting exemplary process is illustrated in the following scheme:

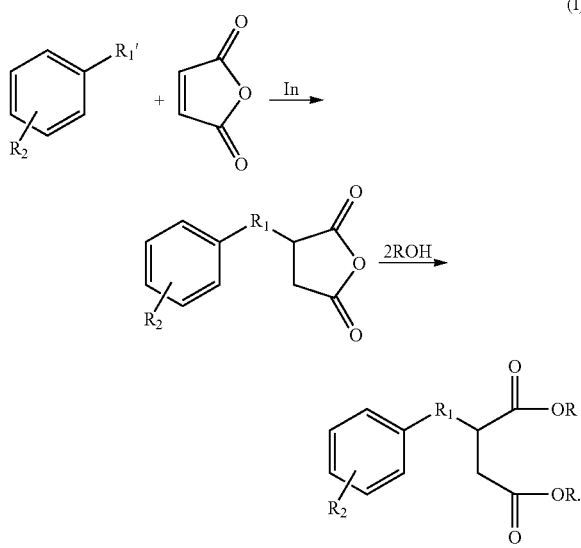

Alternatively, the plasticizer can be produced from esterification of the aromatic anhydride made by double carboxylation of phenyl or benzyl oxirane as demonstrated by Rowley et al., "Catalytic Double Carbonylation of Epoxides to Succinic Anhydrides: Catalyst Discovery, Reaction Scope, and Mechanism", J. Am. Chem. Soc., vol. 129, pp. 4948-4960 (2007), incorporated herein by reference, and illustrated in the following scheme:

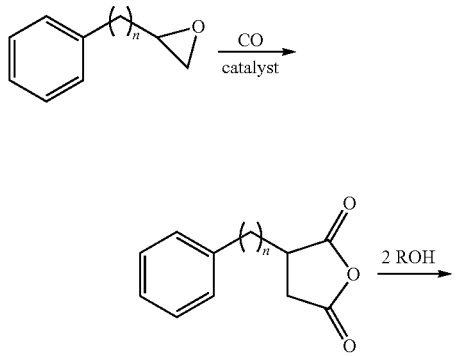

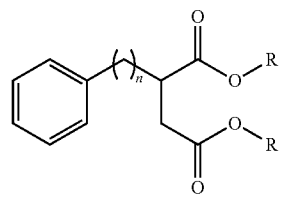

wherein n is 0 or 1 and R represents hydrocarbon residues of $C_4$ to $C_{13}$ OXO-alcohols.

In another embodiment, aromatic compounds can be made from arylation or benzylation of malonic esters, as illustrated in the following scheme:

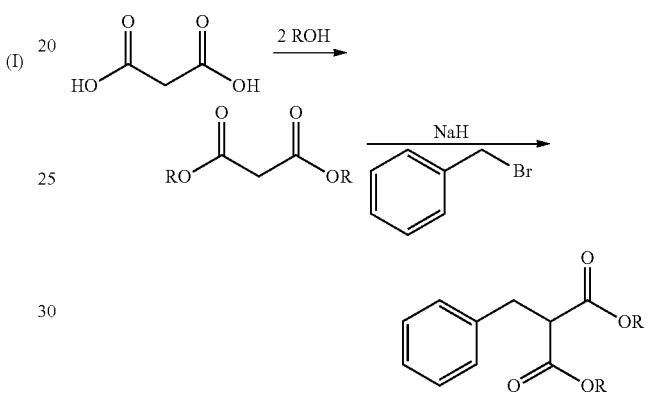

wherein R represents hydrocarbon residues of $C_4$ to $C_{13}$ OXO-alcohols.

In another embodiment, the aromatic compound can be made by copper catalyzed arylation of dialkyl malonate following the protocol of Hennessy and Buchwald, "A General and Mild Copper-Catalyzed Arylation of Diethyl Malonate", Org. Lett. vol. 4, pp. 269-272 (2002), incorporated herein by reference, as shown in the following scheme:

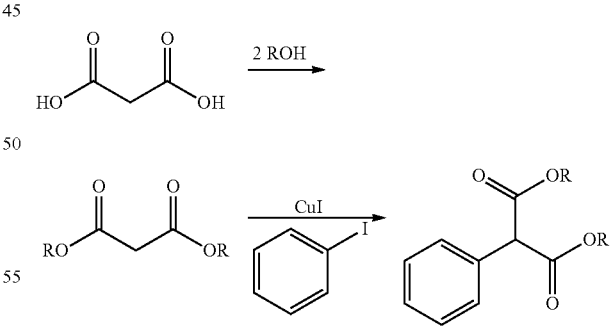

wherein R represents hydrocarbon residues of $C_4$ to $C_{13}$ OXO-alcohols.

In another embodiment, the aromatic compound can be made from the dicarboalkoxylation of styrene as first described by Heck, "Dicarboalkoxylation of Olefins and Acetylenes", J. Am. Chem. Soc. vol. 94, pp. 2712-2716 (1972), incorporated herein by reference, followed by transesterification as illustrated in the following scheme:

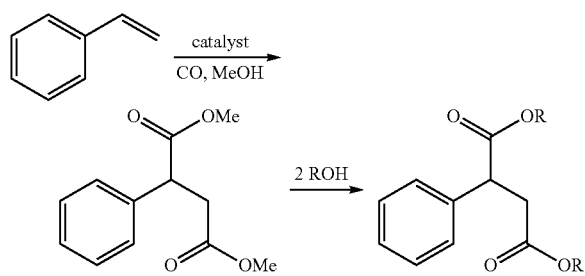

wherein R represents hydrocarbon residues of $C_4$ to $C_{13}$ OXO-alcohols.

In another embodiment, the aromatic compound can be biphenyl, made from 2 moles of benzene, which is then alkylated with, for example an olefin such as ethylene, followed by alkylation of the alkyl-substituent with free radicals formed from an unsaturated cyclic anhydride, which anhydride moiety is then esterified with OXO $C_4$-$C_{13}$ alcohols, according to the process below and as described in the following: 1. For high conversion process for production of cyclohexylbenzene: U.S. Pat. No. 7,579,511, incorporated herein by reference, and 2. For benzene coupling: Ukhopadhyay, Sudip; Rothenberg, Gadi; Gitis, Diana; Sasson, Yoel, Casali Institute of Applied Chemistry, Hebrew University of Jerusalem, Israel; Journal of Organic Chemistry (2000), 65(10), 3107-3110; Publisher: American Chemical Society, incorporated herein by reference.

OXO-alcohols can be prepared by hydroformylating olefins, followed by hydrogenation to form the alcohols. "Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process. The resulting OXO-alcohols consist of multiple isomers of a given chain length due to the various isomeric olefins obtained in the oligomerization process, described below, in tandem with the multiple isomeric possibilities of the hydroformylation step.

Typically, the isomeric olefins are formed by light olefin oligomerization over heterogenous acid catalysts, such as by propylene and/or butene oligomerization over solid phosphoric acid or zeolite catalysts. The light olefins are readily available from refinery processing operations. The reaction results in mixtures of longer-chain, branched olefins, which are subsequently formed into longer chain, branched alcohols, as described below and in U.S. Pat. No. 6,274,756, incorporated herein by reference in its entirety. Olefins for hydroformulation can also be prepared by dimerization of propylene or butenes through commercial processes such as the IFP Dimersol™ process or the Huls (Evonik) Octol™ process.

Branched aldehydes are then produced by hydroformylation of the isomeric olefins. The resulting branched aldehydes (II)

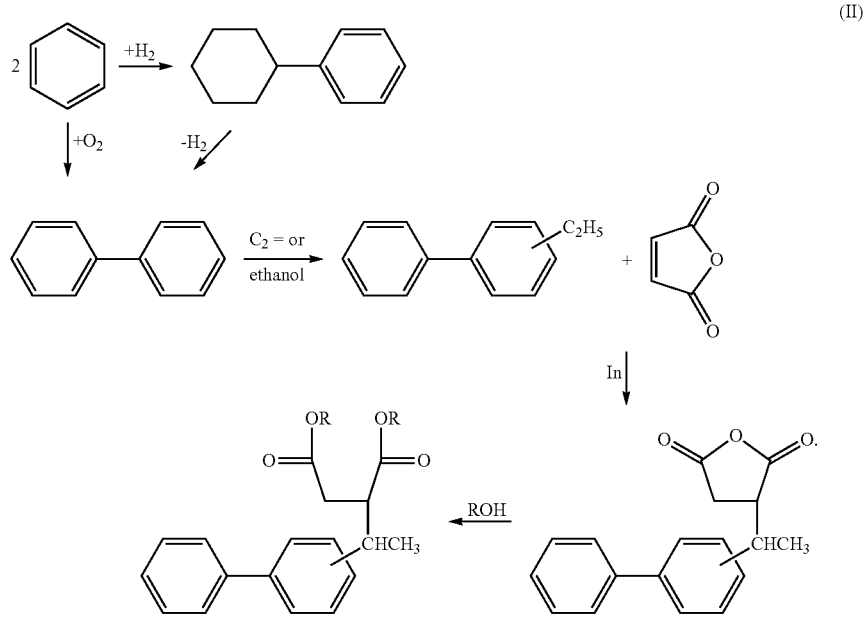

Esterification can be performed according to conventional processes, such as by condensation reaction of OXO-alcohol(s), the formation of which is described in more detail below, with the anhydride moiety of the molecules.

"OXO-alcohols" are isomeric mixtures of branched, organic alcohols. "OXO-esters" are compounds having at least one functional ester moiety within its structure derived from esterification of a carboxylic acid or anhydride portion or moiety of a compound with an OXO-alcohol.

can then be recovered from the crude hydroformylation product stream by fractionation to remove unreacted olefins. These branched aldehydes can then be hydrogenated to form alcohols (OXO-alcohols). Single carbon number alcohols can be used in the esterification of the anhydrides described above, or differing carbon numbers can be used to optimize product cost and performance requirements. The "OXO" technology provides cost advantaged alcohols. Other options are considered, such as hydroformylation of $C_4$-olefins to C$_5$-aldehydes, followed by hydrogenation to C$_5$-alcohols, or aldehyde dimerization followed by hydrogenation to C$_{10}$ alcohols.

"Hydrogenating" or "hydrogenation" is addition of hydrogen (H$_2$) to a double-bonded functional site of a molecule, such as the addition of hydrogen to the aldehyde moieties to form the corresponding alcohol. Conditions for hydrogenation of an aldehyde are well known in the art and include, but are not limited to, temperatures of 0-300° C., pressures of 1-500 atmospheres, and the presence of homogeneous or heterogeneous hydrogenation catalysts such as, but not limited to, Pt/C, Pt/Al$_2$O$_3$ or Pd/Al$_2$O$_3$ and Ni.

Alternatively, the OXO-alcohols can be prepared by aldol condensation of shorter-chain aldehydes to form longer chain aldehydes, as described in U.S. Pat. No. 6,274,756, followed by hydrogenation to form the OXO-alcohols.

"Esterifying" or "esterification" is reaction of a carboxylic acid moiety, such as an anhydride, with an organic alcohol moiety to form an ester linkage. Esterification conditions are well-known in the art and include, but are not limited to, temperatures of 0-300° C., and the presence or absence of homogeneous or heterogeneous esterification catalysts such as Lewis or Brønsted acid catalysts.

As discussed above, the resulting OXO-alcohols can be used individually or together in alcohol mixtures having different chain lengths, or in isomeric mixtures of the same carbon chain length to make mixed esters for use as plasticizers. This mixing of carbon numbers and/or levels of branching can be advantageous to achieve the desired compatibility with PVC for the respective core alcohol used for the polar moiety end of the plasticizer, and to meet other plasticizer performance properties. The preferred OXO-alcohols are those having from 5 to 10 carbons, more preferably C$_5$ to C$_9$ alcohols, and even more preferably C$_6$ to C$_7$ alcohols.

In one embodiment the preferred OXO-alcohols are those which have an average branching of from about 0.8 to about 3.0 branches per molecule, or from about 0.8 to about 1.8 branches per molecule, such as between about 0.8 to about 1.6 branches per molecule, or between about 1.1 to about 1.8 branches per molecule, or about 1.2 to about 1.4 branches per molecule.

Typical branching characteristics of OXO-alcohols are provided in Table 1 below.

In general, for every polymer to be plasticized, a plasticizer is required with the correct balance of solubility, volatility and viscosity to have acceptable plasticizer compatibility with the resin. In particular, if the 20° C. kinematic viscosity is higher than about 250 mm$^2$/sec as measured by the appropriate ASTM test, or alternately if the 20° C. cone-and-plate viscosity is higher than about 250 cP, this will affect the plasticizer processability during formulation, and can require heating the plasticizer to ensure good transfer during storage and mixing of the polymer and the plasticizer. Volatility is also a very critical factor which affects the long-term plasticizer formulation stability. Highly volatile plasticizers can migrate from the plastic resin matrix and cause damage to the article. The plasticizer volatility in a resin matrix can be roughly predicted by neat plasticizer weight loss at 220° C. using Thermogravimetric Analysis.

The present invention discloses unexpected structure-property relationships arising from the addition of specific substituents to the aromatic ring of the aromatic acid/anhydride fragment of the plasticizer molecule, and/or by esterification of the acid/anhydride fragment with mixed alcohol isomers, such as OXO-alcohols. These manipulations allow for the preparation of novel plasticizers having improved volatility-viscosity balances. OXO-alcohols provide a better balance of compatibility and volatility compared to linear alcohols of the same carbon length.

In an alternative embodiment, the aromatic compound can be a hydrocarbon-substituted aromatic compound:

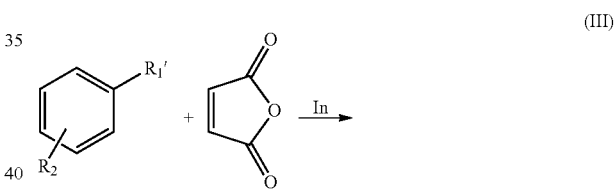

(III)

TABLE 1

$^{13}$C NMR Branching Characteristics of Typical OXO-Alcohols.

| OXO-Alcohol | Avg. Carbon No. | % of α-Carbons w/ Branches$^a$ | β-Branches per Molecule$^b$ | Total Methyls per Molecule$^c$ | Pendant Methyls per Molecule$^d$ | Pendant Ethyls per Molecule |
|---|---|---|---|---|---|---|
| C$_4$$^e$ | 4.0 | 0 | 0.35 | 1.35 | 0.35 | 0 |
| C$_5$$^f$ | 5.0 | 0 | 0.30 | 1.35 | 0.35 | 0 |
| C$_6$ | — | — | — | — | — | — |
| C$_7$ | 7.2 | 0 | 0.13 | 2.2 | — | 0.04 |
| C$_8$ | 8.0 | 0 | 0.08 | 2.6 | — | — |
| C$_9$ | 9.3 | 0 | 0.09 | 3.1 | — | — |
| C$_{10}$ | 10.1 | 0 | 0.08 | 3.1 | — | — |
| C$_{12}$ | 11.8 | 0 | 0.09 | 3.9 | — | — |
| C$_{13}$ | 12.7 | 0 | 0.09 | 3.9 | — | — |

— Data not available.
$^a$—COH carbon.
$^b$Branches at the —CCH$_2$OH carbon.
$^c$This value counts all methyl groups, including C$_1$ branches, chain end methyls, and methyl endgroups on C$_{2+}$ branches.
$^d$C$_1$ branches only.
$^e$Calculated values based on an assumed molar isomeric distribution of 65% n-butanol and 35% isobutanol (2-methylpentanol).
$^f$Calculated values based on an assumed molar isomeric distribution of 65% n-pentanol, 30% 2-methylbutanol, and 5% 3-methylbutanol.

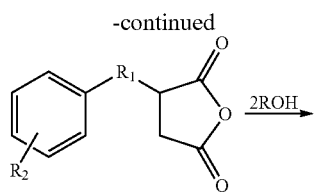

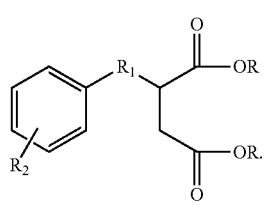

In this case, $R_2$ can be a hydrocarbon substituent, such as an alkyl, an alkylene chain containing one or more oxygen or sulfur atoms, or a cyclic hydrocarbyl, such as a cyclo-$C_5$ or $C_6$ hydrocarbyl, including cycloaliphatic substituents, aromatic substituents such as phenyl, or even a cycloaliphatic or aromatic substituent containing one or more oxygen or sulfur atoms. In preferred embodiments, $R_2$ is —$C_2H_5$ or phenyl. Those skilled in the art will recognize that many such $R_2$ hydrocarbyl-substituted reactants, such as toluene, ethyl benzene, xylenes and cumene, can be obtained in suitably pure forms from existing refinery and/or chemical manufacturing processes.

Substituent $R_1'$, which can be a $C_1$ to $C_6$ alkyl, preferably a $C_2$ to $C_6$ alkyl, is added by an alkylation reaction between the $R_2$-substituted aromatic with a $C_1$ to $C_5$ alkyl under alkylation conditions, such as Friedel-Crafts alkylation with an alkyl halide in the presence of a Lewis acid catalyst. In the alternative, the alkylation can be conducted between the $R_2$-substituted aromatic and olefins or alcohols in the presence of an acid catalyst, such as a zeolite from the MCM family, large pore faujasites, medium pore ZSM-5, or even mixed metal oxides such as $WO_3/ZrO_2$. The reaction conditions for such alkylation reactions are well known in the art and need not be repeated here.

In a particularly advantageous embodiment, the hydrocarbyl-substituted aromatic reactant can be biphenyl, formed by reacting two moles of benzene, such as by reaction in the presence of oxygen, or by reaction in the presence of hydrogen to form cyclohexyl benzene followed by dehydrogenation. The biphenyl reactant is subsequently alkylated, as described above, followed by the initiated radical alkylation with maleic anhydride and esterification of the anhydride moiety with OXO-alcohols, as illustrated below.

(IV)

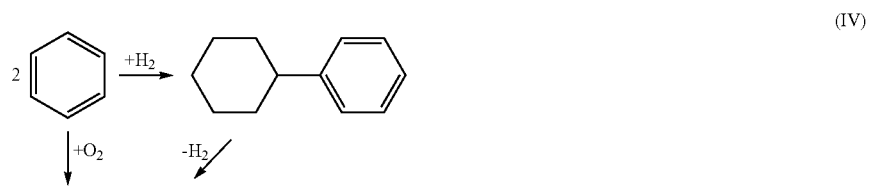

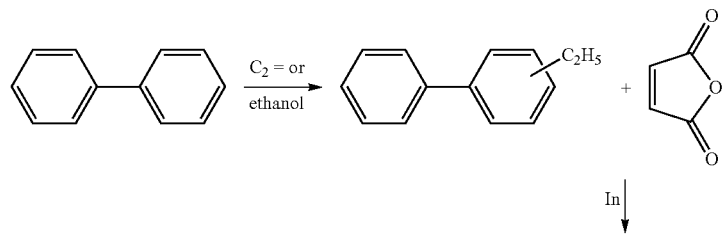

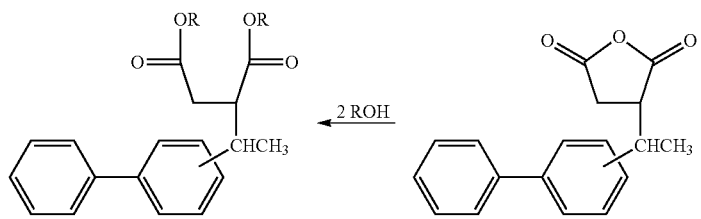

The use of such readily available and inexpensive starting reactants can provide significant cost advantages in the manufacture of non-phthalate plasticizers.

We have found that when $C_5$ to $C_9$ OXO-alcohols are used as reactants for the esterification reactions described above, the resulting OXO-esters are in the form of relatively high-boiling liquids (having low volatility), which are readily incorporated into polymer formulations as plasticizers.

Polymers which can be suitably plasticized with the OXO-esters described herein include thermoplastic polymers such as vinyl chloride resins, polyesters, polyurethanes, ethylene-vinyl acetate copolymer, rubbers, poly(meth)acrylics and combinations thereof.

The following are examples of the present disclosure and are not to be construed as limiting.

EXAMPLES

Examples 1-27 below demonstrate conditions for initiated free radical alkylation of various aromatic compounds with maleic anhydride.

Example 1

Cumene+Maleic Anhydride Radical Alkylation Using Air

To a 500 ml round bottom flask fitted with a mechanical stirrer, thermometer, air inlet bubbler and reflux condenser was added 70.2 g (0.58 moles) of cumene and 8.0 g (0.08 moles) of maleic anhydride. The solution was sparged with air then heated to 145° C. to initiate maleic anhydride free radical formation and then stirred for 6 hr. GC samples were taken at 2, 4 and 6 hr.

Example 2

O-Xylene+Maleic Anhydride Radical Alkylation Using Air

To a 500 ml round bottom flask fitted with a mechanical stirrer, thermometer, air inlet bubbler and reflux condenser was added 65 g (0.61 moles) of o-xylene and 8.0 g (0.08 moles) of maleic anhydride. The solution was sparged with air then heated to reflux to initiate maleic anhydride free radical formation and then stirred for 6 hr. GC samples were taken at 2, 4 and 6 hr.

Example 3

O-Xylene+Maleic Anhydride Radical Alkylation Using NHPI & Air

To a 500 ml round bottom flask fitted with a mechanical stirrer, thermometer, air inlet bubbler and reflux condenser was added 65 g (0.61 moles) of o-xylene, 8.0 g (0.08 moles) of maleic anhydride and 0.073 g of n-hydroxyphthalimide (NHPI) to initiate maleic anhydride free radical formation. The solution was sparged with air and then heated to reflux and stirred for 6 hr. GC samples were taken at 2, 4 and 6 hr.

Example 4

O-Xylene+Maleic Anhydride Radical Alkylation Using tert-Butylperoxide

In a 500 ml round bottom flask fitted with a mechanical stirrer, thermometer, addition funnel and reflux condenser was added 50 g (0.47 moles) of o-xylene. In the addition funnel was added 28.0 g (0.26 moles) of o-xylene and 0.1 ml tert-butylperoxide to initiate maleic anhydride free radical formation. The contents of the addition funnel were added in 2 ml batches along with 2 g batches of maleic anhydride totaling 25.6 g (0.26 moles). Total addition time was 2 hr 45 min.

Example 5

P-Xylene+Maleic Anhydride Radical Alkylation Using tert-Butylperoxide

The experimental procedure was the same as Example 4, except for the substitution of p-xylene for o-xylene.

Example 6

Toluene+Maleic Anhydride Radical Alkylation Using tert-Butylperoxide

To a 500 ml round bottom flask fitted with a mechanical stirrer, thermometer, addition funnel and reflux condenser was added 43.3 g (0.47 moles) of toluene. To the addition funnel was added 24.0 g (0.26 moles) of o-xylene and 0.0794 g tert-butylperoxide to initiate maleic anhydride free radical formation. The contents of the addition funnel were added in 2 ml batches along with 2 g batches of maleic anhydride totaling 25.6 g (0.26 moles). Total addition time was 2 hr 45 min.

Example 7

Toluene+Maleic Anhydride Radical Alkylation Using Air Parr Reactor 125 g (1.36 moles) of toluene and 13.3 g (0.136 moles) of maleic anhydride were weighed into a 300 ml Parr reactor. The reactor was heated to 180° C. then pressurized to 60 psi with air to initiate maleic anhydride free radical formation. The solution was stirred at 180° C. for 4 hr. The reactor was cooled to room temperature, and then the contents were transferred to a round bottom flask. The toluene and maleic anhydride were removed with a rotary evaporator. Weight of residue was 1.4 g.

Example 8

O-Xylene+Maleic Anhydride Radical Alkylation Using Air Pan Reactor

The experimental procedure was the same as for Example 7, except that the air pressure was increased to 100 psig, and o-xylene was substituted for toluene.

Example 9

Toluene+Maleic Anhydride Radical Alkylation Using Air Parr Reactor

The experimental procedure was the same as for Example 7, except that the air pressure was increased to 136 psi.

Example 10

Toluene+Maleic Anhydride Radical Alkylation Using Air Parr Reactor

The experimental procedure was the same as for Example 7, except that the air pressure was increased to 100 psi.

Example 11

Toluene+Maleic Anhydride Radical Alkylation Using AIBN

To a 500 ml round bottom flask fitted with a mechanical stirrer, thermometer, and reflux condenser was added 250 g (2.71 moles) of toluene, 25 g (0.25 moles) of maleic anhydride and 0.25 g of azobisisobutyronitrile (AIBN) to initiate maleic anhydride free radical formation. The solution was heated to reflux and stirred for 6 hr. GC samples were taken at 2, 4 and 6 hr.

Example 12

Toluene+Maleic Anhydride Radical Alkylation Using AIBN Inert Conditions

31.6 g (0.34 moles) of toluene, 3 g (0.03 moles) of maleic anhydride and 0.0313 g AIBN were placed into a sealed reactor bottle. The bottle was placed into an oil bath set at a temperature of 120° C. Samples were taken at 0, 2, 4 and 6 hr.

Example 13

Toluene+Maleic Anhydride Radical Alkylation Using tert-Butylperoxide Inert Conditions

The experimental procedure was the same as for Example 12, except that 1.15 g of t-butylperoxide was substituted for AIBN to initiate maleic anhydride free radical formation.

Example 14

Toluene+Maleic Anhydride Radical Alkylation Using tert-Butylperoxide Inert Conditions

The experimental procedure was the same as for Example 12, except that the amount of t-butylperoxide was decreased to 0.0467 g.

Example 15

Toluene+Maleic Anhydride Radical Alkylation Using tert-Butylperoxide Inert Conditions

The experimental procedure was the same as for Example 12, except that the amount of maleic anhydride was decreased to 2.17 g and the amount of t-butylperoxide was increased to 0.5890 g.

Example 16

Toluene+Maleic Anhydride Radical Alkylation Using tert-Butylperoxide Inert Conditions Metering

11.7 g (0.13 moles) of toluene, and 0.3702 g (0.003 moles) of t-butylperoxide were placed into a sealed reactor bottle. The bottle was placed into an oil bath set at a temperature of 120° C. In a syringe was placed 19.7 g (0.21 moles) toluene, 4.06 g (0.041 moles) maleic anhydride and 0.7877 g (0.005 moles) t-butyl peroxide. The contents of the syringe were added to the reactor at 5 ml/min Total delivery time was 5 hr. Samples were taken at 0, 3, 5, 6 and 7 hr.

Example 17

Toluene+Maleic Anhydride Radical Alkylation Using tert-Butylperoxide Inert Conditions Metering

80 g (0.87 moles) of toluene, and 1.17 g (0.008 moles) t-butylperoxide were placed into a sealed reactor bottle. The bottle was placed into an oil bath set at a temperature of 120° C. In a syringe was placed 20.13 g (0.22 moles) toluene, and 4.10 g (0.042 moles) maleic anhydride. The contents of the syringe were added to the reactor at 5 ml/min Total delivery time was 5 hr. Samples were taken at 0, 3, 5, 6 and 7 hr.

Example 18

Toluene+Maleic Anhydride Radical Alkylation Using AIBN Inert Conditions

34.0 g (0.37 moles) of toluene, 4.2 g (0.04 moles) of maleic anhydride and 1.2970 g AIBN were placed into a sealed reactor bottle. The bottle was placed into an oil bath set at a temperature of 90° C. Samples were taken at 0, 2, 4 and 6 hr.

Example 19

Toluene+Maleic Anhydride Radical Alkylation Using tert-Butylperoxide Inert Conditions Metering

30.3 g (0.33 moles) of toluene, and 4.06 g (0.04 moles) maleic anhydride were placed into a sealed reactor bottle. The bottle was placed into an oil bath set at a temperature of 120° C. In a syringe was placed 1.2 g (0.012 moles) toluene, and 1.1637 g (0.008 moles) t-butylperoxide. The contents of the syringe were added to the reactor at 5 ml/min Total delivery time was 5 hr. Samples were taken at 0, 3, 5, 6 and 7 hr.

Example 20

Cumene+Maleic Anhydride Radical Alkylation Using tert-Butylperoxide Inert Conditions

42.8 g (0.37 moles) of cumene, 4.18 g (0.04 moles) of maleic anhydride and 1.1405 g (0.008 moles) t-butylperoxide were placed into a sealed reactor bottle. The bottle was placed into an oil bath set at a temperature of 120° C. Samples were taken at 0, 2, 4 and 6 hr.

Example 21

Ethylbenzene+Maleic Anhydride Radical Alkylation Using Tert-Butylperoxide Inert Conditions

42.6 g (0.37 moles) of ethyl benzene, 4.18 g (0.04 moles) of maleic anhydride and 1.1405 g (0.008 moles) t-butylperoxide were placed into a sealed reactor bottle. The bottle was placed into an oil bath set at a temperature of 120° C. Samples were taken at 0, 2, 4 and 6 hr.

Example 22

Cumene+Maleic Anhydride Radical Alkylation Using tert-Butylperoxide Inert Conditions Metering 19.15 g (0.16 moles) of cumene, and 4.11 g (0.04 moles) maleic anhydride were placed into a sealed reactor bottle. The bottle was placed into an oil bath set at a temperature of 120° C. In a syringe was placed 19.2 g (0.16 moles) cumene, and 1.1527 g (0.008 moles) t-butyl peroxide. The contents of the syringe were added to the reactor at 5 ml/min Total delivery time was 5 hr. Samples were taken at 0, 3, 5, 6 and 7 hr.

Example 23

Cumene+Maleic Anhydride Radical Alkylation Using tert-Butylperoxide

To a 2 liter round bottom flask fitted with a mechanical stirrer, thermometer, and $N_2$ inlet bubbler was added 1000 g (8.3 moles) of cumene and 100 g (1.02 moles) of maleic anhydride and 20 g (0.137 moles) t-butyl peroxide. The solution was sparged with $N_2$ then heated to 120° C. and stiffed for 6 hr. The solution was cooled, and then excess cumene was removed by distillation to give 214.6 g of a crude product. The product was vacuum distilled at 130° C. and 0.07 mmHg yielding 138.7 g product.

Example 24

Ethylbenzene+Maleic Anhydride Radical Alkylation Using tert-Butylperoxide

To a 2 liter round bottom flask fitted with a mechanical stirrer, thermometer, and $N_2$ inlet bubbler was added 750 g (7.1 moles) of ethyl benzene, 100 g (1.02 moles) of maleic anhydride and 20 g (0.137 moles) t-butyl peroxide. The solution was sparged with $N_2$ then heated to 120° C. and stirred for 6 hr. The solution was cooled, and then excess ethyl benzene was removed by distillation to give a crude product. The product was vacuum distilled at 120° C. and 0.05 mmHg yielding 178.6 g product.

Example 25

Cumene+Maleic Anhydride Radical Alkylation Using Cumene Hydroperoxide

In a 2 liter round bottom flask fitted with a mechanical stirrer, thermometer, and $N_2$ inlet bubbler was added 750 g (6.2 moles) of cumene, 100 g (1.02 moles) of maleic anhydride and 15.45 g (0.10 moles) cumene hydroperoxide. The solution was sparged with $N_2$ then heated to 120° C. and stirred for 6 hr. The solution was cooled, and then excess cumene was removed by distillation to give a crude product. The product was vacuum distilled at 130° C. with 0.07 mmHg yielding 80% product.

Example 26

Ethylbenzene+Maleic Anhydride Radical Alkylation Using tert-Butylperoxide

To a 2 liter round bottom flask fitted with a mechanical stirrer, thermometer, and $N_2$ inlet bubbler was added 750 g (7.1 moles) of ethyl benzene. The solution was sparged with $N_2$, heated to 120° C. and then 20 g (0.14 moles) t-butylperoxide was added, followed by 3 hourly additions of 35 g (total of 105 g, 1.07 moles) of maleic anhydride and was stirred for a total of 6 hr. Excess ethyl benzene was removed by distillation.

Example 27

Cumene+Maleic Anhydride Radical Alkylation Using tert-Butylperoxide

To a 2 liter round bottom flask fitted with a mechanical stirrer, thermometer, and $N_2$ inlet bubbler was added 1000 g (8.3 moles) of ethyl benzene. The solution was sparged with $N_2$, heated to 120° C. and then 25 g (0.17 moles) t-butylperoxide was added, followed by 4 hourly additions of 35 g (total of 140 g, 1.43 moles) of maleic anhydride and was stirred for a total of 6 hr. Excess cumene was removed by distillation.

Example 28

Diethylbenzene+Maleic Anhydride Radical Alkylation Using tert-Butylperoxide

To a 2 liter round bottom flask fitted with a mechanical stirrer, thermometer, and $N_2$ inlet bubbler was added 750 g (10.25 moles) of diethyl benzene. The solution was sparged with $N_2$, heated to 120° C. and then 15 g (0.1 moles) t-butylperoxide was added, followed by 9 hourly additions of 30 g (total of 270 g, 2.75 moles) of maleic anhydride and was stirred for a total of 7 hr. wt of distilled product 445 g. Excess diethyl benzene was removed by distillation.

Example 29

Benzylbromide+Diisononyl Malonate

Diisononyl malonate (56 mmol) was dissolved in THF and cooled to 0° C.

Sodium hydride (61.6 mmol) was added in portions and the suspension stiffed for 30 min Benzyl bromide (56 mmol) was then added slowly and the reaction allowed to warm to ambient temperature. The reaction was quenched with saturated ammonium chloride and the layers separated. The aqueous layer was extracted 3 times with ethyl acetate and combined organic layers washed with brine, dried over $MgSO_4$, and concentrated under reduced pressure to give the benzylated malonate as a pale yellow oil. Purification was achieved by vacuum distillation: $^1H$ NMR (400 MHz, $C_6D_6$) δ 0.89 (m, 34 H), 3.24 (d, J=8.0 Hz, 2 H), 3.68 (m, 1 H), 4.11 (m, 4 H), 7.28 (m, 5 H).

Example 30

Benzylbromide+Diisoheptylmalonate

Made from diheptyl malonate and benzylbromide as described above for diisononyl 1-benzylmalonate: $^1H$ NMR (400 MHz, $C_6D_6$) δ 0.87-1.56 (m, 26 H), 3.24 (m, 2 H), 3.67 (m, 1 H), 4.10 (m, 4 H), 7.26 (m, 5 H); $^{13}C$ NMR (100 MHz, $C_6D_6$) 11.5-39.3 (13 C), 54.0, 65.7, 66.1, 126.9, 128.6 (2 C), 129.0 (2 C), 130.3, 138.1, 169.1 (2C).

Example 31

Condensation of 2-phenylmalonate and Oxo-$C_9$ Alcohol

2-Phenylmalonic acid and Oxo-$C_9$ (2 equiv) were dissolved in toluene.

Several drops of sulfuric acid were added and the reaction heated at reflux with removal of water by a Dean-Stark trap. Upon completion of the condensation, toluene was removed and diisononyl 2-phenylmalonate was purified by vacuum distillation: $^1H$ NMR (400 MHz, $C_6D_6$) δ 0.86-1.64 (34 H), 4.15 (m, 4 H), 4.62 (m, 1 H), 7.36 (m,5 H); $^{13}C$ NMR (100 MHz, $C_6D_6$) 12.5-36.3 (16 C), 58.3, 66.1, 66.4, 128.3, 128.7 (2 C), 129.5 (2 C), 133.1, 168.4 (2 C).

Example 32

Condensation of 2-phenylmalonate and OXO-$C_9$ Alcohol

2-Phenylmalonic acid and OXO-$C_7$ (2 equiv) were dissolved in toluene. Several drops of sulfuric acid were added and the reaction heated at reflux with removal of water by a Dean-Stark trap. Upon completion of the condensation, toluene was removed and diheptyl 2-phenylmalonate was purified by vacuum distillation: $^1H$ NMR (400 MHz, $C_6D_6$) δ 0.86-1.64 (m, 24 H), 4.16 (m, 4 H), 4.63 (s, 1 H), 7.37 (m, 5 H); $^{13}C$ NMR (100 MHz, $C_6D_6$) 11.2-39.1 (12 C), 58.1, 65.8, 66.2, 128.1, 128.5 (2 C), 129.3 (2 C), 132.9, 168.2 (2 C).

General Procedure for Esterification

To a four-necked 1000 ml round bottom flask equipped with an air stirrer, nitrogen inductor, thermometer, Dean-Stark trap and chilled water cooled condenser were added x mole of acid and y mole of OXO-alcohols. The reaction mixture was heated to certain temperature ° C. with air stirring under a nitrogen sweep. The water collected in the Dean-Stark trap was drained frequently and monitored until approximately theoretical weight was collected, indicating near complete reaction. The excess alcohols were removed by distillation. The conditions for each of the following examples are summarized in Table 2, below.

Examples 33-48 below demonstrate conditions for esterification of the various compounds formed in Examples 1-27, except as otherwise indicated.

Example 33

Esterification of Phenyl Succinic Acid with OXO-$C_9$ Alcohols

To a 4-necked 500 ml round bottom flask equipped with an air stiffer, thermometer, $N_2$ inductor, Dean-Stark trap and chilled water cooled condenser were added phenyl succinic acid (100 g, 0.515 mole), and OXO-$C_9$ alcohols (222.9 g, 1.545 moles). The reaction mixture was heated at 168-219° C. for 4 hours with GC sampling. The product was distilled using a Claisen adapter, chilled water cooled condenser and receiving flask. The product was distilled overhead, Bp=199-200° C./0.10 mm. The purity obtained by GC was 99.6%.

Example 34

Esterification of 3-phenyl Glutaric Acid with OXO-$C_7$ Alcohols

To a 4-necked 500 ml round bottom flask equipped with an air stiffer, thermometer, $N_2$ inductor, Dean-Stark trap and chilled water cooled condenser were added 3-phenyl glutaric acid (25 g, 0.12 mole), and (41.9 g, 0.36 mole). The reaction mixture was heated at 175-176° C. for 7 hours with GC sampling. The product was concentrated using a Claisen adapter, chilled water cooled condenser and receiving flask. The concentrated product was a clear yellow liquid. The purity obtained was 95% by GC.

Example 35

Esterification of Benzyl Succinic Anhydride with OXO-$C_9$ Alcohols

To a 4-necked 500 ml round bottom flask equipped with an air stiffer, thermometer, $N_2$ inductor, Dean-Stark trap and chilled water cooled condenser were added benzyl succinic anhydride (15.1 g, 0.08 mole), OXO-$C_9$ alcohols (115.4 g, 0.8 mole) and xylenes (79.9 g, 0.75 mole). The reaction mixture was heated for a total of 25 hours at 151-170° C. with GC sampling. The product was then distilled using a Claisen adapter, chilled water cooled condenser and receiving flask. The product distilled at 210-222° C./0.10 mm and was a clear orange liquid, 97.1% purity by GC.

Example 36

Esterification of Cumyl Succinic Anhydride with OXO-$C_9$ Alcohols

To a 4-necked 1000 ml round bottom flask equipped with an air stirrer, thermometer, $N_2$ inductor, Dean-Stark trap and chilled water cooled condenser were added cumyl succinic anhydride (110.4 g, 0.506 mole), OXO-$C_9$ alcohols (309.1 g, 2.143 mole) and xylenes (13.3 g, 0.13 mole). The reaction mixture was heated for a total of 22 hours at 209-214° C. with GC sampling. The excess alcohols were then removed by distillation using a Claisen adapter, chilled water cooled condenser and receiving flask. The concentrated product was treated with decolorizing charcoal at room temperature with magnetic stiffing for 2 hours. A clear light yellow product with a purity of 99.2% by GC was obtained.

Example 37

Esterification of Ethyl Benzene Succinic Anhydride with OXO-$C_9$ Alcohols

To a 4-necked 500 ml round bottom flask equipped with an air stiffer, thermometer, $N_2$ inductor, Dean-Stark trap and chilled water cooled condenser were added ethyl benzene succinic anhydride (66.13 g, 0.331 mole), OXO-$C_9$ alcohols (190.72 g, 1.323 mole) and xylenes (53.5 g, 0.504 mole). The reaction mixture was heated for a total of 20 hours at 182-188° C. with GC sampling. The product was concentrated using a Claisen adapter, chilled water cooled condenser and receiving flask. The concentrated product (133.3 g) was dissolved in toluene (62 g) and was washed twice with 50 g of a 3 wt % sodium hydroxide solution followed by distilled water (50 g). The upper toluene phase was then dried over magnesium sulfate, filtered and concentrated. The hazy product and was filtered twice with filter aid to obtain a clear and colorless liquid. The purity was 99.5% by GC diester.

Example 38

Esterification of Ethyl Benzene Succinic Anhydride with OXO-$C_7$ Alcohols

To a 4-necked 500 ml round bottom flask equipped with an air stiffer, thermometer, $N_2$ inductor, Dean-Stark trap and chilled water cooled condenser were added ethyl benzene succinic anhydride (51.75 g, 0.2588 mole), OXO-$C_7$ alcohols (120.44 g, 1.04 mole) and xylenes (27.0 g, 0.254 mole). The reaction mixture was heated a total of 72 hours at 169-189° C. with GC sampling. The product was concentrated using a Claisen adapter, chilled water cooled condenser and receiving flask. The concentrated product was dissolved in an equal weight of toluene (99 g) and was washed twice with 50 g of a 3 wt % sodium hydroxide solution followed by distilled water (50 g). The upper toluene phase was then dried over magnesium sulfate, filtered and treated with decolorizing charcoal. The product was distilled with a Claissen head, which distilled at Bp=160-167° C./0.05 mm. The purity obtained by GC analysis was 99.8%. On standing the distillate became hazy and was filtered twice with a filter aid to obtain a clear and colorless liquid.

Example 39

Esterification of Ethyl Benzene Succinic Anhydride with $C_5$ Alcohols

To a 4-necked 500 ml round bottom flask equipped with an air stiffer, thermometer, $N_2$ inductor, Dean-Stark trap and chilled water cooled condenser were added ethyl benzene succinic anhydride (50 g, 0.25 mole), $C_5$ alcohols (65/35, 1-pentanol/2-methylbutanol) (56.11 g, 0.64 mole 1-pentanol and 30.21 g, 0.342 mole 2-methyl-1-butanol). The reaction mixture was heated at total of 20 hours at 136-185° C. with GC sampling. The product was then distilled using a Claisen adapter, chilled water cooled condenser and receiving flask. The product distilled at 155-157° C./0.10 mm and was a clear and colorless liquid, 32.9 g. The main fraction was dissolved in an equal weight of toluene (32.9 g) and was washed twice with 33 g of a 3 wt % sodium hydroxide solution followed by distilled water (33 g). The upper toluene phase was then dried over magnesium sulfate, filtered and concentrated using a rotary evaporator. The product was obtained was 99.7% pure by GC analysis.

Example 40

Esterification of Cumyl Succinic Anhydride with OXO-$C_7$ Alcohols

To a 4-necked 500 ml round bottom flask equipped with an air stirrer, thermometer, $N_2$ inductor, Dean-Stark trap and chilled water cooled condenser were added cumyl succinic anhydride (34.04 g, 0.1598 mole) and OXO-$C_7$ alcohols (72.6 g, 0.624 mole). Additional OXO-$C_7$ alcohols (28.1 g, 0.24 mole) were added to the Dean-Stark trap. The reaction mixture was heated at total of 39 hours at 180-192° C. with GC sampling. The product was concentrated using a Claisen adapter, chilled water cooled condenser and receiving flask. The concentrated product was dissolved in an equal weight of toluene (60.4 g) and was washed twice with 30 g of a 3 wt % sodium hydroxide solution followed by distilled water (25 g) twice. The upper toluene phase was then dried over magnesium sulfate, filtered and concentrated using a rotary evaporator. The product was hazy and was filtered twice with a filter aid to obtain a clear and colorless liquid. The purity of the diester product was 99.2% by GC.

Example 41

Esterification of Cumyl Succinic Anhydride with $C_5$ Alcohols (65/35, 1-pentanol/2-methyl-1-butanol To a 4-necked 500 ml round bottom flask equipped with an air stiffer, thermometer, $N_2$ inductor, Dean-Stark trap and chilled water cooled condenser were added cumyl succinic anhydride (43.0 g, 0.201 mole), $C_5$ alcohols at a ratio of 65/35 1-pentanol/2-methyl-1-butanol (70.87 g, 0.809 mole). The mixed normal and branched alcohols were used to simulate OXO-alcohols. Additional $C_5$ alcohols (22 g, 0.25 mole) (65/35 ratio) were added to the Dean-Stark trap. The reaction mixture was heated for a total of 43 hours at 138-167° C. with GC sampling. The product was concentrated using a Claisen adapter, chilled water cooled condenser and receiving flask. The concentrated product was dissolved in an equal weight of toluene (63 g) and was washed twice with 30 g of a 3 wt % sodium hydroxide solution followed by distilled water (30 g) twice. The upper toluene phase was then dried over magnesium sulfate, filtered and concentrated using a rotary evaporator. The product was distilled overhead, Bp=150° C./0.10 mm. The purity obtained was 99.32% by GC.

Example 42

Esterification of tert-butyl Ethyl Benzene Succinic Anhydride with $C_6$ Alcohols (65/35, 1-hexanol/2-methyl-1-pentanol)

To a 4-necked 500 ml round bottom flask equipped with an air stirrer, thermometer, $N_2$ inductor, Dean-Stark trap and chilled water cooled condenser were added tert-butyl ethyl benzene succinic anhydride (35.0 g, 0.1314 mole) and $C_6$ alcohols at a ratio of 65/35 1-hexanol/2-methyl-1-pentanol (53.7 g, 0.526 mole). The mixed normal and branched alcohols were used to simulate OXO-alcohols. Additional $C_6$ alcohols (21 g, 0.21 mole) (65/35 ratio) were added to the Dean-Stark trap and toluene (50 g, 0.54 mole). The reaction mixture was heated at 125° C. for 28 hours with GC sampling. Complete conversion was not obtained so the temperature was allowed to rise to 150° C. resulting in distillation and removal of the toluene. The reaction mixture was heated an additional 24 hours at 150° C. The product was concentrated using a Claisen adapter, chilled water cooled condenser and receiving flask. The concentrated product was dissolved in an equal weight of toluene (30 g) and was washed twice with 20 g of a 3 wt % sodium hydroxide solution followed by distilled water (20 g) twice. The upper toluene phase was then dried over magnesium sulfate, filtered and concentrated using a rotary evaporator. The product was distilled overhead, Bp=180° C./0.10 mm. The purity obtained was 97.7% by GC.

Example 43

Esterification of 1,4-diisopropyl Benzene Succinic Anhydride with $C_6$ Alcohols (65/35, 1-hexanol/2-methyl-1-pentanol)

To a 4-necked 500 ml round bottom flask equipped with an air stirrer, thermometer, $N_2$ inductor, Dean-Stark trap and chilled water cooled condenser were added 1,4-diisopropyl benzene succinic anhydride (98.6 g, 0.387 mole) and $C_6$ alcohols at a ratio of 65/35 1-hexanol/2-methyl-1-pentanol (158.41 g, 1.55 mole). The mixed normal and branched alcohols were used to simulate OXO-alcohols. The reaction mixture was heated at 165-197° C. for 14 hrs, 92% of the theoretical water was removed from the Dean-Stark trap during this heating period. The product was concentrated using a Claisen adapter, chilled water cooled condenser and receiving flask. The concentrated product was dissolved in an equal weight of toluene (170.6 g) and was washed twice with 50 g of a 3 wt % sodium hydroxide solution followed by distilled water (50 g) twice. The upper toluene phase was then dried over magnesium sulfate, filtered and distilled. The product was distilled overhead, Bp=213° C./0.10 mm. The purity obtained was 99.2% by GC.

Example 44

Esterification of Ethyl Benzene Succinic Anhydride with $C_6$ alcohols (65/35 1-hexanol/2-methyl-1-pentanol)

To a 4-necked 500 ml round bottom flask equipped with an air stirrer, thermometer, $N_2$ inductor, Dean-Stark trap and chilled water cooled condenser were added ethyl benzene succinic anhydride (26.0 g, 0.13 mole) and $C_6$ alcohols at a ratio of 65/35 1-hexanol/2-methyl-1-pentanol (53.13 g, 0.52 mole). The mixed normal and branched alcohols were used to simulate OXO-alcohols. The reaction mixture was heated at 157-171° C. for 29 hours with GC sampling. The product was concentrated using a Claisen adapter, chilled water cooled condenser and receiving flask. The concentrated product was dissolved in an equal weight of toluene (40.3 g) and was washed twice with 15 g of a 3 wt % sodium hydroxide solution followed by distilled water (15 g) twice. The upper toluene phase was then dried over magnesium sulfate, filtered and concentrated using a rotary evaporator. The product was distilled overhead, Bp=174-180° C./0.10 mm. The purity obtained was 99.8% by GC.

Example 45

Esterification of Cumyl Succinic Anhydride with $C_6$ Alcohols (65/35, 1-hexanol/2-methyl-1-pentanol)

To a 4-necked 500 ml round bottom flask equipped with an air stirrer, thermometer, $N_2$ inductor, Dean-Stark trap and chilled water cooled condenser were added cumyl succinic anhydride (102.8 g, 0.458 mole) and $C_6$ alcohols at a ratio of 65/35 1-hexanol/2-methyl-1-pentanol (187.1 g, 1.83 mole). The mixed normal and branched alcohols were used to simulate OXO-alcohols. The reaction mixture was heated at 160-164° C. for 29 hours with GC sampling. The product was concentrated using a Claisen adapter, chilled water cooled condenser and receiving flask. The concentrated product was dissolved in an equal weight of toluene (140.6 g) and was washed twice with 75 g of a 3 wt % sodium hydroxide solution followed by distilled water (75 g) twice. The upper toluene phase was then dried over magnesium sulfate, filtered and concentrated using a rotary evaporator. The concentrated product was distilled overhead, Bp=182° C./0.10 mm The purity obtained was 99.7%.

Example 46

Esterification of Ethyl Benzene Succinic Anhydride with 1-heptanol (Comparative)

Into a 4-necked 500 ml round bottom flask equipped with an air stiffer, thermometer, $N_2$ inductor, Dean-Stark trap and chilled water cooled condenser were added ethyl benzene succinic anhydride (88.63 g, 0.4431 mole) and 1-heptanol (205.8 g, 1.773 mole). The reaction mixture was heated at 184-193° C. for 11 hours with GC sampling. The product was concentrated using a Claisen adapter, chilled water cooled condenser and receiving flask. The concentrated product was dissolved in an equal weight of toluene (163.8 g) and was washed twice with 75 g of a 3 wt % sodium hydroxide solution followed by distilled water (75 g) twice. The upper toluene phase was then dried over magnesium sulfate, filtered and concentrated using a rotary evaporator. The product was distilled overhead, Bp=189° C./0.10 mm. The purity obtained was 99.1% by GC.

Example 47

Esterification of Cumyl Succinic Anhydride with 1-heptanol (Comparative)

To a 4-necked 500 ml round bottom flask equipped with an air stirrer, thermometer, $N_2$ inductor, Dean-Stark trap and chilled water cooled condenser were added cumyl succinic anhydride (96.03 g, 0.4509 mole) and 1-heptanol (209.33 g, 1.803 mole). The reaction mixture was heated at 185-203° C. for 26 hours with GC sampling. The product was concentrated using a Claisen adapter, chilled water cooled condenser and receiving flask. The concentrated product was dissolved in an equal weight of toluene (182.9 g) and was washed twice with 75 g of a 3 wt % sodium hydroxide solution followed by distilled water (75 g) twice. The upper toluene phase was then dried over magnesium sulfate, filtered and then distilled. The product was distilled overhead, Bp=220° C./0.10 mm. The purity obtained was 99.2% by GC.

Example 48

Esterification of 2-(4-methoxy)phenyl)succinic acid with OXO-$C_9$ Alcohols

To a 4-necked 500 ml round bottom flask equipped with an air stirrer, thermometer, $N_2$ inductor, Dean-Stark trap and chilled water cooled condenser were added 2-(4-methoxy) phenyl)succinic acid (99.7 g, 0.4447 mole) and OXO-$C_9$ alcohols (193.03 g, 1.334 moles). The reaction mixture was heated at 177-220° C. for 7 hours with GC sampling. The excess alcohols were distilled using a Claisen adapter, chilled water cooled condenser and receiving flask. The crude product was treated with 2 wt % decolorizing charcoal at 22° C. with stirring for 16 hr. The mixture was filtered twice. The purity obtained was 99.6% by GC.

TABLE 2

Summary of conditions for forming different esters at ambient pressure

| Sample # | Acid or Anhydride | Alcohol | Temp ° C. | Purity, % (by GC) |
|---|---|---|---|---|
| DINP* | Phthalic anhydride | OXO $C_9$ | 220 | |
| 33 | Phenyl succinic acid | OXO $C_9$ | 168-219 | 99.6 |
| 34 | 43-phenyl glutaric acid | OXO $C_7$ | 175-176 | 95.0 |
| 35 | Benzyl succinic anhydride | OXO $C_9$ | 151-170 | 97.1 |
| 36 | Cumyl succinic anhydride | OXO $C_9$ | 209-214 | 99.2 |
| 37 | Ethyl benzene succinic anhydride | OXO $C_9$ | 182-188 | 99.5 |
| 38 | Ethyl benzene succinic anhydride | OXO $C_7$ | 169-189 | 99.8 |
| 39 | Ethyl benzene succinic anhydride | $C_5$ (65/35) n-pentanol/ 2-methylbutanol | 136-185 | 99.7 |
| 40 | Cumyl succinic anhydride | OXO $C_7$ | 180-192 | 97.2 |
| 41 | Cumyl succinic anhydride | $C_5$ (65/35) n-pentanol/ 2-methylbutanol | 138-167 | 99.3 |

TABLE 2-continued

Summary of conditions for forming different esters at ambient pressure

| Sample # | Acid or Anhydride | Alcohol | Temp ° C. | Purity, % (by GC) |
|---|---|---|---|---|
| 42 | tert-butyl ethyl benzene succinic anhydride | C₆ alcohols (65/35, 1-hexanol/2-methyl-1-pentanol | 125-150 | 97.7 |
| 43 | 1,4-diisopropyl benzene succinic anhydride | C₆ alcohols (65/35, 1-hexanol/2-methyl-1-pentanol | 165-176 | 99.2 |
| 44 | Ethyl benzene succinic anhydride | C₆ alcohols (65/35, 1-hexanol/2-methyl-1-pentanol | 157-171 | 99.8 |
| 45 | Cumyl succinic anhydride | C₆ alcohols (65/35, 1-hexanol/2-methyl-1-pentanol | 160-164 | 99.7 |
| 46 | Ethyl benzene succinic anhydride | 1-heptanol | 184-193 | 99.1 |
| 47 | Cumyl succinic anhydride | 1-heptanol | 185-203 | 99.7 |
| 48 | 2-(4-methoxy)phenyl succinic acid | Oxo-C₉ | 177-220 | 99.6 |

*diisononyl phthalate

Example 52

General Esterification Procedure for Diethyl Benzene Succinic Anhydride Plus Alcohol To a 4-necked round bottom reaction flask equipped with an air stirrer, thermometer, nitrogen inductor, Dean-Stark trap and reflux condenser were added the diethyl benzene succinic anhydride (example 28) plus the alcohols. The reaction mixture was heated at reflux while removing the water from the Dean-Stark trap. At the completion of the reaction, excess alcohols were removed by vacuum distillation from the crude product. The crude product was then diluted in toluene and washed with 3% aqueous sodium hydroxide followed by distilled water washing. The upper toluene phase was then dried over 10 wt % magnesium sulfate, filtered and the product was distilled under vacuum. The following table provides detail for the alcohols tested:

TABLE 3

| Examples # | Diethyl-benzene succinic anhydride, (moles) | OXO-Alcohols | Alcohols, (moles) | Run Temp. C. | Heating Time, (hours) | Purity of Diester (%) by GC |
|---|---|---|---|---|---|---|
| 49 | 0.26 | 5 | 1.05 | 138-220 | 44 | 99.85 |
| 50 | 0.68 | 6 | 2.70 | 147-162 | 119 | 99.80 |
| 51 | 0.33 | 7 | 1.30 | 170-174 | 39 | 99.23 |
| 52 | 0.53 | 9 | 2.10 | 193-220 | 23 | 99.20 |

Differential Scanning calorimetry (DSC), Viscosity, and Thermogravimetric Analysis (TGA) Property Study of Neat Esters Thermogravimetric Analysis (TGA) was conducted on the neat esters using a TA Instruments TGA Q5000 instrument (25-450° C., 10° C./min, under 25 cc $N_2$/min flow through furnace and 10 cc $N_2$/min flow through balance; sample size approximately 10 mg). Table 4, below, provides a volatility comparison of the different esters. Differential Scanning calorimetry (DSC) was also performed on the neat esters, using a TA Instruments Q2000 calorimeter fitted with a liquid $N_2$ cooling accessory. Samples were loaded at room temperature and cooled to about −130° C. at 10° C./min and analyzed on heating to 75° C. at a rate of 10° C./min. Table 4 provides a glass transition ($T_g$) comparison of the different esters. $T_g$s given in Table 4 are midpoints of the first heats (unless only one heat cycle was performed, in which case the first heat $T_g$, which is typically in very close agreement, is given). Kinematic Viscosity (KV) was measured at 20° C. according to ASTM D-445-20; results are summarized in Table 4. Comparative data for a common commercial plasticizer (di-isononyl phthalate; Jayflex® DINP, ExxonMobil Chemical Co.) is also included.

TABLE 4

Volatility, Viscosity, and Glass Transition Properties of Neat Esters

| Ex. No. | TGA 1% Wt Loss (° C.) | TGA 5% Wt Loss (° C.) | TGA 10% Wt Loss (° C.) | TGA Wt Loss at 220° C. (%) | DSC $T_g$ (° C.) | KV (20° C., mm²/sec) |
|---|---|---|---|---|---|---|
| DINP | 184.6 | 215.2 | 228.5 | 6.4 | −79.1 | 96.8 |
| 33 | 189.5 | 218.4 | 233.6 | 5.3 | −78.9 | 91.9 |
| 34 | — | — | — | — | — | — |
| 35 | — | — | — | — | — | — |
| 36 | 197.9 | 233.2 | 249.3 | 2.7 | −60.0 | 376.5 |
| 37 | 189.2 | 226.0 | 242.4 | 3.8 | −67.1 | 197.2 |
| 38 | 175.0 | 206.6 | 221.7 | 9.2 | −72.7 | 94.3 |
| 39 | 152.6 | 184.1 | 198.8 | 25 | −75.4 | 63.0 |
| 40 | 179.7 | 210.5 | 225.5 | 7.8 | −65.9 | 166.6 |
| 41 | 153.3 | 184.6 | 199.9 | 23 | −67.2 | 117.5 |
| 42 | 172 | 204.2 | 220 | 10 | −67.3 | 179.8 |
| 43 | 178.5 | 213.2 | 229.4 | 6.7 | −74.8 | 201.1 |
| 44 | 162.7 | 194.1 | 209.4 | 15.7 | −77.7 | 193.3 |
| 45 | 166.8 | 197.5 | 212.4 | 13.8 | −70.2 | 117.2 |
| 46 | 178.7 | 211.9 | 227.6 | 7.2 | −81.1 | 63.7 |
| 47 | 179.6 | 213.4 | 230.7 | 6.5 | −74.8 | 103.8 |
| 48 | 209.4 | 242.2 | 259 | 1.7 | −66.8 | 193.3 |
| 49 | 210.18 | 239.3 | 254.25 | 1.786 | −65.0 | 71.1 |
| 50 | 173.1 | 202.3 | 216.5 | 11.8 | −75.5 | 81.1 |
| 51 | — | — | — | — | — | 102.3 |
| 52 | — | — | — | — | — | 208.0 |

— = Data not taken.

General Procedures for the Use of Esters to Plasticize Poly (Vinyl Chloride)

Example 53

Method for Preparation of Plasticized Polymer Testing Bars by Solvent Method

A 5.85 g portion of the ester sample (or comparative commercial plasticizer DINP) was weighed into an Erlenmeyer flask which had previously been rinsed with uninhibited tetrahydrofuran (THF) to remove dust. A 0.82 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 117 mL uninhibited THF. Oxy Vinyls® 240F PVC (11.7 g) was added in powdered form and the contents of the flask were stirred overnight at room temperature until dissolution of the PVC was complete. The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, typically almost colorless film was carefully peeled away and exhibited no oiliness or inhomogeneity unless otherwise noted. The film was cut into small pieces to be used for preparation of test bars by compression molding (size of pieces was similar to the hole dimensions of the mold plate). The film pieces were stacked into the holes of a multi-hole steel mold plate, preheated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™-coated aluminum foil and the following multistage press procedure was used at 170° C. with no release between stages: (1) 3 minutes with 1-2 ton overpressure; (2) 1 minute at 10 tons; (3) 1 minute at 20 tons; (4) 1 minute at 30 tons; (5) 3 additional minutes at 30 tons; (6) release and 3 minutes in the cooling stage of the press (7° C.) at 30 tons. A knockout tool was then used to remove the sample bars with minimal flexion. Typically near-colorless, flexible bars were obtained which, when stored at room temperature, showed no oiliness exudation after pressing unless otherwise noted. The bars were allowed to age at room temperature for at least 1 week prior to evaluation of phase behavior with Differential Scanning calorimetry (DSC) and thermo-physical properties with Dynamic Mechanical Thermal Analysis (DMTA).

Example 54

Method for Preparation of Plasticized Polymer Testing Bars by Melt Mixing Method In a 250 ml beaker is added 2.7 g of an additive package containing a 70/30 wt/wt of Paraplex G62 ESO/Mark 4716. To this is added 19.1 g of plasticizer and the mixture is stirred with a spatula until blended. After blending, 38.2 g of PVC is added and the mixture is mixed, forming a paste. The mixture is added to the melt mixture. A Haake Rheomix 600 mixer manufactured by Haake PolyLab System is preheated to the desired mixing temperature (165° C. for most experiments). A coarsely mixed sample consisting of plasticizer, polyvinylchloride and stabilizers is added to the mixer while stirring at 35 rpm. After addition the mixer is stopped for one minute. The mixer is started again and the sample is mixed for five minutes. After mixing for five minutes the mixer is stopped and disassembled. The mixed sample is removed hot.

98° C. Weight Loss Comparison of PVC Bars Plasticized with Esters Versus PVC Bars Plasticized with Commercial Plasticizer Two each of the PVC sample bars prepared above were placed separately in aluminum weighing pans and placed inside a convection oven at 98° C. Initial weight measurements of the hot bars and measurements taken at specified time intervals were recorded and results were averaged between the bars. The averaged results are shown in Table 5. Notes on the appearance and flexibility of the bars at the end of the test are also given.

TABLE 5

98° C. % Weight Loss of Ester-Containing PVC Bars and DINP-Containing PVC Control Bars.

| Example No. (Ester Used in Bar) | Day 1 | Day 7 | Day 14 | Day 21 | Notes on Bar |
|---|---|---|---|---|---|
| DINP[1] | 0.31 | 0.48 | 0.64 | 0.74 | Light brown; good flex |
| 33[1] | Na | 0.213 | 0.303 | na | Oily, mod. stiff |
| 34[1] | Na | na | na | na | Still flexible |
| 35[1] | 0.172 | 0.321 | 0.489 | 0.612 | Still good flex ~/ sl. <DINP dark brown |
| 36[1] | 0.145 | 0.239 | — | 0.342 | Exudates after one day, oily surface, very stiff |
| 37[1] | 0.224 | 0.345 | 0.434 | 0.484 | Exudates after one day, oily surface, dark brown, flex |
| 38[1] | 0.1888 | 0.732 | 1.101 | 1.659 | Light brown, different phases |
| 39[1] | 0.369 | 3.703 | 4.986 | 7.578 | Dark brown, very stiff |
| 40[1] | 0.277 | 0.543 | 1.125 | 1.369 | Yellow brownish, flex |
| 41[1] | 0.588 | 2.196 | 4.044 | 5.287 | Stiff, yellow brown, clear, homogenous phase |
| 42[2] | 0.381 | 0.777 | 1.242 | 1.704 | Yellow brown, flex |
| 43[2] | 0.166 | 0.359 | | | Exudates, oily surface, a bit stiff |
| 44[2] | 0.407 | 1.038 | 3.763 | | Soft, yellow brownish |
| 45[2] | 0.361 | 0.905 | 1.733 | | Soft, little brown |
| 46[2] | 0.255 | 0.477 | 0.750 | | Very flex, yellow brown |
| 47[2] | 0.256 | 0.543 | 0.728 | | Very flex, yellow brown |
| 48[2] | | | | | Stiff |
| 49[2] | 0.279 | 1.103 | 2.514 | 5.770 | Soft, clear |
| 50[2] | 0.214 | 0.512 | 0.853 | 1.148 | Soft, yellow brownish |
| 51[2] | 0.223 | 0.486 | 0.690 | 0.775 | Soft |
| 52[2] | 0.175 | 0.267 | 0.322 | 0.320 | exudates |

[1]Bars made following example 53 method
[2]Bars made following example 54 method 70° C. Humid Aging Clarity Comparison of PVC Bars Plasticized with Esters Versus PVC Bars Plasticized with Commercial Plasticizer.

Using a standard one-hole office paper hole punch, holes were punched in two each of the sample bars prepared above about ⅛" from one end of the bar. The bars were hung in a glass pint jar (2 bars per jar) fitted with a copper insert providing a stand and hook. The jar was filled with ~½" of distilled water and the copper insert was adjusted so that the bottom of each bar was ~1" above the water level. The jar was sealed, placed in a 70° C. convection oven, and further sealed by winding Teflon™ tape around the edge of the lid. After 21 days the jars were removed from the oven, allowed to cool for ~20 minutes, opened, and the removed bars were allowed to sit under ambient conditions in aluminum pans (with the bars propped at an angle to allow air flow on both faces) or hanging from the copper inserts for 14 days (until reversible humidity-induced opacity had disappeared). The bars were evaluated visually for clarity. All bars exhibited complete opacity during the duration of the test and for several days after removal from the oven. Results are shown in Table 6. Notes on the appearance and flexibility of the bars at the end of the test are also given.

TABLE 6

70° C. Humid Aging Clarity and Appearance properties of Ester- and DINP-Containing PVC Bars.

| Example No. (Ester Used in Bar) | Notes on Bar |
|---|---|
| DINP[1] | A little stiff, clear |
| 33[1] | Very stiff, oily |
| 34[1] | Good flex, sticky, fingerprints |

TABLE 6-continued

70° C. Humid Aging Clarity and Appearance properties of Ester- and DINP-Containing PVC Bars.

| Example No. (Ester Used in Bar) | Notes on Bar |
|---|---|
| 35[1] | Stiff, very oily, still opaque |
| 36[1] | V. stiff, oily and cloudy |
| 37[1] | Little bit stiff, oily and cloudy |
| 38[1] | Good flex but little bit cloudy |
| 39[1] | Good flex but little bit cloudy |
| 40[1] | Sticky surface, cloudy, stiff |
| 41[1] | Sticky surface, cloudy, stiff |
| 42[2] | A bit stiff, |
| 43[2] | Sticky surface, stiff and cloudy |
| 44[2] | Sticky surface, flex clear |
| 45[2] | Sticky surface, Good flex |
| 46[2] | Sticky surface, Good flex |
| 47[2] | Sticky surface, Good flex |
| 48[2] | Stiff, oily |
| 49[2] | A little bit stiff, brownish |
| 50[2] | Clear good flex |
| 51[2] | Clear good flex |
| 52[2] | exudates |

[1]Bars made following example 53 method
[2]Bars made following example 54 method

Example 55

Demonstration of Plasticization of PVC with Esters Via Thermogravimetric Analysis (TGA) and Differential Scanning Calorimetry (DSC)

Thermogravimetric Analysis (TGA) was conducted on the neat esters using a TA Instruments TGA5000 instrument (25-450° C., 10° C./min, under 25 cc $N_2$/min flow through furnace and 10 cc $N_2$/min flow through balance; sample size approximately 10 mg). Table 7 provides a volatility comparison of the neat and plasticized PVC bars. Differential Scanning calorimetry (DSC) was performed on the compression-molded sample bars (PVC: plasticizer ratio 2:1) using a TA Instruments Q2000 calorimeter fitted with a liquid $N_2$ cooling accessory. Samples were loaded at room temperature and cooled to approximately −90° C. at 10° C./min, and then analyzed on heating at a rate of 10° C./min to 100-150° C. for plasticized PVC bars, and to 100° C. for the comparative neat PVC bar. Small portions of the sample bars (typical sample mass 5-7 mg) were cut for analysis, making only vertical cuts perpendicular to the largest surface of the bar to preserve the upper and lower compression molding "skins"; the pieces were then placed in the DSC pans so that the upper and lower "skin" surfaces contacted the bottom and top of the pan. Table 8 provides the first heat $T_g$ onset, midpoint, and end for neat PVC and the plasticized bars. A lowering and broadening of the glass transition for neat PVC is observed upon addition of the esters, indicating plasticization and extension of the flexible temperature range of use for neat PVC (for aid in calculating the numerical values of these broad transitions, the DSC curve for each plasticized bar was overlaid with the analogous Dynamic Mechanical Thermal Analysis (DMTA) curve, since the DMTA curve provides additional guidance about the proper temperature regions for the onset, midpoint, and end of $T_g$).

TABLE 7

Volatility Properties of Neat PVC and PVC Sample Bars Containing Plasticizers

| Ex. No. | TGA 1% Wt Loss (° C.) | TGA 5% Wt Loss (° C.) | TGA 10% Wt Loss (° C.) | TGA % Wt Loss at 220° C. |
|---|---|---|---|---|
| NONE (neat PVC) | 129.9 | 192.3 | 255.4 | 6.3 |
| DINP[1] | 204.6 | 247.4 | 257.6 | 1.8 |
| 33[1] | 207.1 | 246.5 | 256.5 | 1.7 |
| 34[1] | — | — | — | — |
| 35[1] | — | — | — | — |
| 36[1] | 218.5 | 251.4 | 262.7 | 1.1 |
| 37[1] | 212 | 251.2 | 260.5 | 1.3 |
| 38[1] | 192.2 | 231.3 | 250.3 | 3.2 |
| 39[1] | 171.3 | 206.1 | 236.9 | 7.3 |
| 40[1] | 195.6 | 237.5 | 252.8 | 2.8 |
| 41[1] | 175.6 | 215 | 247.4 | 5.7 |
| 42[2] | 188.4 | 230.5 | 246.3 | 3.5 |
| 43[2] | — | — | — | — |
| 44[2] | 177.3 | 216.8 | 244 | 5.6 |
| 45[2] | 180.5 | 221.4 | 248.2 | 4.8 |
| 46[2] | 190.2 | 234.9 | 252.9 | 2.8 |
| 47[2] | 196.6 | 239.3 | 254.6 | 2.4 |
| 48[2] | 222.3 | 252.3 | 264.3 | 0.9 |
| 49[2] | 177.2 | 214.3 | 241.1 | 6.0 |
| 50[2] | 186.7 | 226.5 | 245.2 | 4.1 |
| 51[2] | 193.4 | 236.4 | 248.9 | 2.7 |
| 52[2] | 212.7 | 247.3 | 258.3 | 1.3 |

— = Data not taken.

TABLE 8

Glass Transition Onset, Midpoint, and End for Plasticized PVC Bars by DSC.

| Ex. No. | $T_g$ Onset (° C.) | $T_g$ Midpt (° C.) | $T_g$ End (° C.) | $T_m$ Max (° C.) and $DH_f$ (J/g)[a] |
|---|---|---|---|---|
| NONE (neat PVC) | 44.5 | 46.4 | 48.9 | not calc. |
| DINP[1] | −37.8 | −24.8 | −12.2 | not calc. |
| 33[1] | −55.4, 5.3 | −39.0, 9.4 | −22.4, 13.4 | 56.8, 1.1 |
| 34[1] | — | — | — | — |
| 35[1] | — | — | — | — |
| 36[1] | −49.7 | −25.4 | −1.2 | 54.3, 1.3 |
| 37[1] | −52.3, 0.6 | −39.2, 5.3 | −25.8, 9.1 | 56.7, 0.9 |
| 38[1] | −47 | −24.6 | −2.2 | 56.6, 1.2 |
| 39[1] | −47.8 | −26.6 | −5.3 | 57.5, 0.8 |
| 40[1] | −33.8 | −9.4 | 15.3 | 54.5, 1.1 |
| 41[1] | −21.8 | −2.6 | 17.1 | 55.4, 1.0 |
| 42[2] | −45.9 | −24.2 | −2.5 | 54.4, 0.7 |
| 43[2] | — | — | — | — |
| 44[2] | −47 | −20.7 | 5.6 | 54.3, 0.8 |
| 45[2] | −42.2 | −15.2 | 11.8 | 52.9, 0.7 |
| 46[2] | −53.3 | −27.2 | −1 | 54.7, 0.7 |
| 47[2] | −48.7 | −19.4 | 9.8 | 55.1, 0.7 |
| 48[2] | −37.0, 4.5 | −24.7, 10.9 | −10.8, 16.6 | 55.0, 1.0 |
| 49[2] | −43.3 | −22 | −0.8 | 55.5, 1.0 |
| 50[2] | −50.8 | −27.2 | −3.6 | 58.4, 0.5 |
| 51[2] | −53.4 | −32.6 | −11.7 | 53.6, 1.0 |
| 52[2] | −60.2 | −40.9 | −21.7 | 52.6, 0.9 |

— Data not obtained.
[a]Most sample bars showed a weak melting point ($T_m$) from the crystalline portion of PVC. Often this weak transition was not specifically analyzed, but data is given here in instances where it was recorded.

The data in Table 8 provides a measure of the flexibility range of the plasticized PVC specimen, measured by DSC. The range of the glass transition corresponds to the flexibility range. Most advantageous are samples which demonstrate both a broad $T_g$ range (the difference between $T_g$, onset and $T_g$, end) as well as having a low flex onset (as measured by $T_g$, onset).

TABLE 9

Various DMTA Thermal Parameters for
PVC Bars Plasticized with Esters

| Ex. No. | Tan δ $T_g$ Onset (° C.) | Tan δ Peak (° C.) | 25° C. Storage Mod. (MPa) | Temp. of 100 MPa Storage Mod. (° C.) | Flexible Use Range (° C.) |
|---|---|---|---|---|---|
| NONE (neat PVC) | 44.0 | 61.1 | 1433 | 57.1 | 13.1 |
| DINP[1] | −46.7 | 12.6 | 33.3 | 12.2 | 58.9 |
| 33[1] | −44.3 | 45.3 | 118.8 | 27.2 | 71.5 |
| 34[1] | — | — | — | — | — |
| 35[1] | — | — | — | — | — |
| 36[1] | −53.4 | 49.6 | 217.1 | 34.5 | 87.9 |
| 37[1] | −44.2 | 43.6 | 166.8 | 30.4 | 74.5 |
| 38[1] | −46.7 | 18.3 | 46.3 | 15.1 | 61.8 |
| 39[1] | −42.8 | 10.9 | 16.6 | 8.3 | 51.0 |
| 40[1] | −43.4 | 28.1 | 69.4 | 21.3 | 64.7 |
| 41[1] | −43.3 | 25.4 | 62.9 | 20.6 | 63.9 |
| 42[2] | −45.4 | 37.2 | 99.6 | 24.9 | 70.3 |
| 43[2] | — | — | — | — | — |
| 44[2] | −48.7 | 10.2 | 32.3 | 11.0 | 59.7 |
| 45[2] | −44.4 | 20.0 | 50.5 | 17.6 | 62.0 |
| 46[2] | −54.1 | 16.9 | 37.6 | 12.1 | 61.2 |
| 47[2] | −47.4 | 28.8 | 53.0 | 18.2 | 65.6 |
| 48[2] | −39.3 | 46.0 | 222.5 | 34.1 | 73.4 |
| 49[2] | −42.5 | 13.5 | 37.1 | 13.3 | 55.8 |
| 50[2] | −45.9 | 20.4 | 40.7 | 15.0 | 60.9 |
| 51[2] | −47.3 | 28.0 | 57.8 | 19.1 | 66..4 |
| 52[2] | −58.0 | 49.6 | 193.3 | 33.9 | 91.9 |

— Data not obtained.

The data in Table 9 provides a measure of the flexibility range and the mechanical properties of the plasticized PVC specimen. Most advantageous are samples which demonstrate both a flexible range as well as having a low flex onset (as measured by tan δ, onset). Additionally, low storage modulus values at 25° C. are desirable.

Testing shore A hardness, tensile properties, low temperature flexibility, aging of dumbbells, retained tensile strength.

Example 56

A solution was prepared by dissolving 0.5 grams of stearic acid with slight heating and stirring in 100 grams of the plasticizer of this invention, example 38. After the stearic acid dissolved, the solution was cooled to room temperature, and 6.0 grams of the PVC stabilizer Thermcheck™ SP 210 (Ferro) was added. This solution was then added to 200 grams of PVC resin (OXY 240F) and mixed under low speed in a Hobart mixer. The mixture was processed into a flexible PVC product through milling on a Dr. Collins roll mill, at 165° C. for 6 minutes. The milled sheet was removed from the roll mill, cooled to room temperature, and then portions of this product were pressed to test specimens of various thicknesses, at 170° C. for 15 minutes. After cooling, the test specimens were removed from the molds, and aged for 7 days at 22° C., 50% relative humidity.

Testing of this product yielded the following results: Shore A hardness of 77.7, tensile properties (30 mil test specimens, Type C die) gave an ultimate tensile strength of 3382 psi, 100% modulus of 2099 psi, and an ultimate elongation of 339%. Low temperature flexibility as measured by the Clash-Berg procedure gave a temperature of −15° C. No exudation was seen in any of the 100% relative humidity testing up to 7 days or in the ⅜ inch loop test.

Aging of dumbbells, for 7 days, 100 C, with airflow of 150 air changes/hr gave a weight loss of 14%. Retained tensile strength was 86% of the original tensile strength.

By comparison, a DINP formulation prepared under the same conditions and tests gave a Shore A hardness of 79.1, original tensile strength of 3245 psi, 100% modulus of 1982 psi, ultimate elongation of 314%, a Clash-Berg temperature of −17° C. Aging of DINP dumbbells for 7 days at 100° C. gave a weight loss of 7.8% with a retained tensile strength of 98%. No exudation was observed in any of the compatibility tests.

Example 57

As in Example 53 above, a formulation was prepared with 200 grams of PVC resin (OXY 240F), 120 grams of the plasticizer of example 41, 6 grams of PVC stabilizer Thermcheck™ SP 210, and 0.5 grams stearic acid, milled at 165° C. for 6 minutes and then pressed into plaques at 17° C. for 15 minutes. After 7 days at 22° C., 50% relative humidity, the product gave a Shore A Hardness of 67.4 and a Clash-Berg temperature of −24° C.

Example 58

A PVC plastisol was prepared according the ASTM D1755 method, by mixing in a Hobart mixer 150 grams of the plasticizer example 38, 200 grams of PVC resin, and 6 grams of PVC stabilizer Thermcheck™ SP 1363 and at varying speeds for 10 minutes. The 1 hour plastisol viscosity after mixing was 2010 cP. At a shear rate of 180 l/s. DMA fusion temperature was 175° C.; however, the max viscosity was reached at 144° C. By comparison a DINP formulation prepared by the same procedure had a 1 hr plastisol viscosity of 2440 cp. The DINP fusion temperature was about 169° C., but the viscosity build was very rapid in the 85° C.-95° C. temperature range.

Example 59

A solution was prepared by dissolving 4.4 grams of stearic acid with slight heating and stirring in the plasticizer of this invention, example 45. After the stearic acid dissolved, the solution was cooled to room temperature, and 6.0 grams of the PVC stabilizer Thermcheck™ SP 210 (Ferro) was added. This solution was then added to 200 grams of PVC resin (OXY 240F) and mixed under low speed in a Hobart mixer. The mixture was processed into a flexible PVC product through milling on a Dr. Collins roll mill, at 165° C. for 6 minutes. The milled sheet was removed from the roll mill, cooled to room temperature, and then portions of this product were pressed to test specimens of various thickness, at 170° C. for 15 minutes. After cooling, the test specimens were removed from the molds, and aged for 7 days at 22° C., 50% relative humidity.

Testing of this product yielded the following results: Shore A hardness of 79.67, tensile properties (30 mil test specimens, Type C die) gave a ultimate tensile strength of 3487 psi, 100% modulus of 2289 psi, and an ultimate elongation of 296%. Low temperature flexibility as measured by the Clash-Berg procedure gave a temperature of −12° C. No exudation was seen in either of the 100% relative humidity testing up to 7 days or in the ⅜ inch loop test.

Aging of dumbbells, for 7 days, 100° C., with an airflow of 150 air changes/hr gave a weight loss of 20.2%.

Outdoor exposure as estimated by QUV testing using UV-B bulbs showed no discoloration after 4 weeks. By comparison the DINP reference formulation showed slight yellowing beginning after 3 weeks of exposure.

Example 60

As in Example 53 above, a formulation was prepared with 200 grams of PVC resin (OXY 240F), 120 grams of the plasticizer of example 45, 6 grams of PVC stabilizer Thermcheck™ SP 210, and 0.5 grams stearic acid, milled at 165° C. for 6 minutes and then pressed into plaques at 170° C. for 15 minutes. After 7 days at 22° C., 50% relative humidity, the product gave a Shore A Hardness of 68.5 and a Clash-Berg temperature of −23° C. No exudation was observed in any compatibility studies Example 61

A PVC plastisol was prepared according the ASTM D1755 method, by mixing in a Hobart mixer, 150 grams of the plasticizer example 45, 200 grams of PVC resin, and 6 grams of PVC stabilizer Thermcheck™ SP 1363. The 1 hour plastisol viscosity after mixing was 2010 cP. At a shear rate of 180 l/s. DMA fusion temperature was 173° C.; however, the max viscosity was slowly reached at 140° C.

Example 62

A solution was prepared by dissolving 0.5 grams of stearic acid with slight heating and stirring in 100 grams of plasticizer of this invention, example 50. After the stearic acid dissolved, the solution was cooled to room temperature, and 6.0 grams of the PVC stabilizer Thermcheck™ SP 210 (Ferro) was added. This solution was then added to 200 grams of PVC resin (OXY 240F) and mixed under low speed in a Hobart mixer. The mixture was processed into a flexible PVC product through milling on a Dr. Collins roll mill, at 165° C. for 6 minutes. The milled sheet was removed from the roll mill, cooled to room temperature, and then portions of this product were pressed to test specimens of various thickness, at 170° C. for 15 minutes. After cooling, the test specimens were removed from the molds, and aged for 7 days at 22° C., 50% relative humidity.

Testing of this product yielded the following results: Shore A hardness of 87.5, tensile properties (30 mil test specimens, Type C die) gave a ultimate tensile strength of 3492 psi, 100% modulus of 2082 psi, and an ultimate elongation of 323%. No exudation was seen in either of the 100% relative humidity testing up to 7 days or in the ⅜ inch loop test.

Aging of dumbbells, for 7 days, 100° C., with an airflow of 150 air changes/hr gave a weight loss of 16.8%. Retained tensile strength was 130% of the original tensile strength.

A gradual darkening was observed in QUV testing (UV-B bulbs) after 3 weeks.

Example 63

A solution was prepared by dissolving 0.5 grams of stearic acid with slight heating and stirring in 100 grams of plasticizer of this invention, example 51. After the stearic acid dissolved, the solution was cooled to room temperature, and 6.0 grams of the PVC stabilizer Thermcheck™ SP 210 (Ferro) was added. This solution was then added to 200 grams of PVC resin (OXY 240F) and mixed under low speed in a Hobart mixer. The mixture was processed into a flexible PVC product through milling on a Dr. Collins roll mill, at 165° C. for 6 minutes. The milled sheet was removed from the roll mill, cooled to room temperature, and then portions of this product were pressed to test specimens of various thickness, at 170° C. for 15 minutes. After cooling, the test specimens were removed from the molds, and aged for 7 days at 22° C., 50% relative humidity.

Testing of this product yielded the following results: Shore A hardness of 90.4, tensile properties (30 mil test specimens, Type C die) gave a ultimate tensile strength of 3521 psi, 100% modulus of 2215 psi, and an ultimate elongation of 319%. No exudation was seen in either of the 100% relative humidity testing up to 7 days or in the ⅜ inch loop test.

Aging of dumbbells, for 7 days, 100° C., with an airflow of 150 air changes/hr gave a weight loss of 7.3%. Retained tensile strength was 95% of the original tensile strength. A slight discoloration was seen in QUV (UV-B bulbs) after 3 weeks.

Example 64

A PVC plastisol was prepared according the ASTM D1755 method, by mixing in a Hobart mixer, 75 grams of the plasticizer from example 50, 100 grams of PVC resin, and 3 grams of PVC stabilizer Thermcheck™ SP 1363. The 1 hour plastisol viscosity after mixing was 1700 cP. at a shear rate of 210 l/s. DMA gelation maximum viscosity was slowly reached at 155° C. Evaluation of molded test plaques gave a Shore A Hardness of 64.6, a tensile strength of 2201 psi, a 100% modulus of 910 psi, and an ultimate elongation of 390%.

Example 65

A PVC plastisol was prepared according the ASTM D1755 method, by mixing in a Hobart mixer, 75 grams of the plasticizer from example 51, 100 grams of PVC resin, and 3 grams of PVC stabilizer Thermcheck™ SP 1363. The 1 hour plastisol viscosity after mixing was 2000 cP. at a shear rate of 210 l/s. DMA gelation maximum viscosity was slowly reached at 160° C. Evaluation of molded test plaques gave a Shore A Hardness of 67.1, a tensile test of 2818 psi, 100% modulus of 954, and an ultimate elongation of 381%.

PCT and EP Claims:

1. Compounds of the formula:

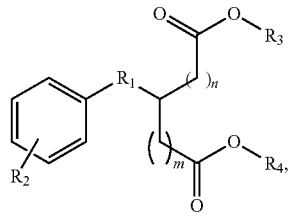

wherein m=0-3, and n=0-3, and $R_1$ represents $C_xH_{2x}$ wherein x=0-4 or cyclohexane; $R_2$ represents H, a $C_1$-$C_6$ alkyl group at any of the ortho-, meta- or para-positions, a residue including heteroatoms chosen from O, N, and S, or mixtures thereof; and $R_3$ and $R_4$ represent hydrocarbon residues of OXO-$C_5$-$C_9$ alcohols which are different isomers of equal carbon number or different in carbon number.

2. The compounds of clause 1, wherein $R_1$ is $C_xH_{2x}$ wherein x=0, $CH_2$, $CH_2$—$CH_2$ or CH—$CH_3$, $CH_2$—$CH_2$—$CH_2$, CH—$CH_2$—$CH_3$, $CH_3$—C—$CH_3$, $CH_3$—$CH_2$—C—$CH_3$, CH—$CH_2$—$CH_2$—$CH_3$, or $CH_2$—$CH_2$—$CH_2$—$CH_2$.

3. The compounds of any one of the preceding clauses, wherein $R_2$ is H, methyl, ethyl, a cyclic $C_5$ or $C_6$ hydrocarbyl.

4. The compounds of any one of the preceding clauses, wherein the $R_2$ is chosen from phenyl, tert-butyl, iso-propyl, and methoxy.

5. The compounds of any one of the preceding clauses, wherein $R_3$ and $R_4$ are hydrocarbon residues of $C_6$-$C_7$ OXO-alcohols.

6. The compound of any one of the preceding clauses, wherein the
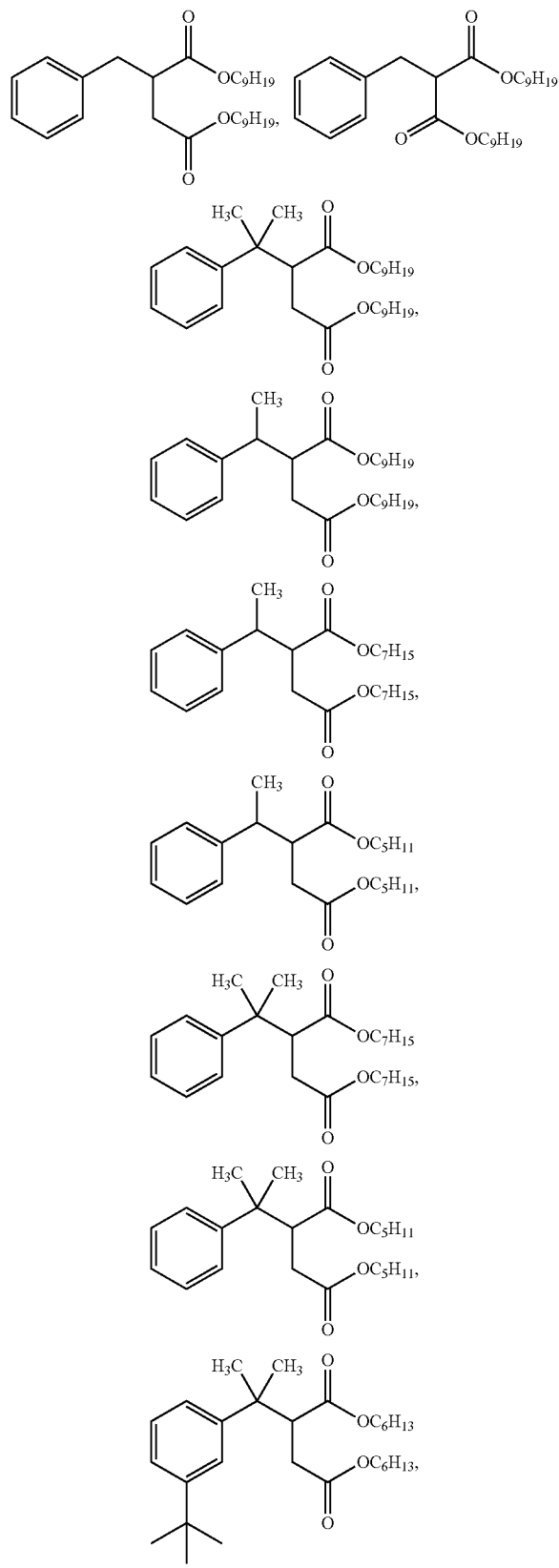
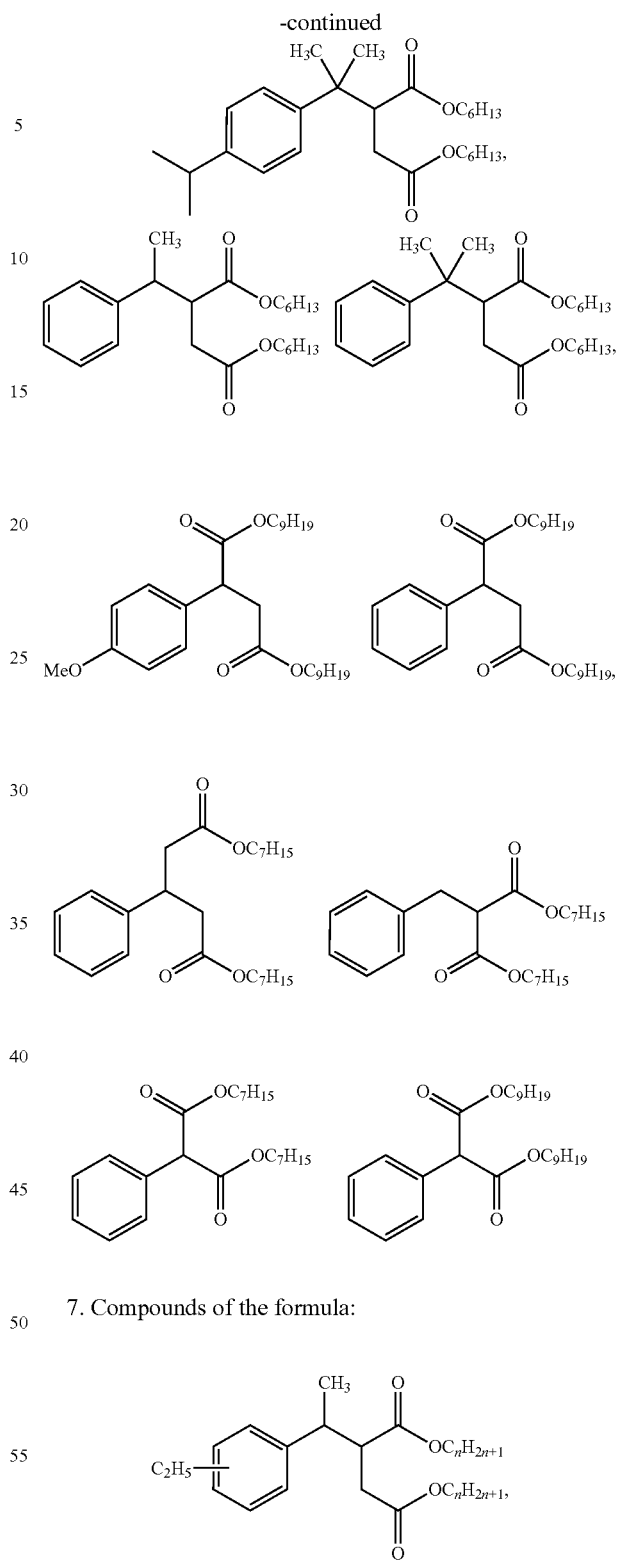
7. Compounds of the formula:
wherein the ethyl substituent (—$C_2H_5$) is in the ortho-, meta- or para-position, or mixtures of these isomers at different ratios, and n=6 or 7.
8. A polymer composition comprising a thermoplastic polymer and at least one plasticizer comprising compounds of the formula:

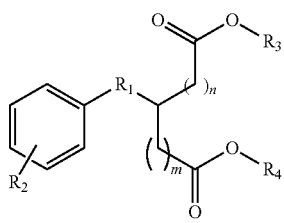

wherein m=0-3, and n=0-3

$R_1$ represents $C_xH_{2x}$ wherein x=0-4 or cyclohexane; $R_2$ represents H, a $C_1$-$C_6$ alkyl group at any of the ortho-, meta- or para-positions, a residue including heteroatoms chosen from O, N, and S, or mixtures thereof; and $R_3$ and $R_4$ represent hydrocarbon residues of OXO-$C_5$-$C_9$ alcohols which are different isomers of equal carbon number or different in carbon number.

9. The polymer composition of clause 8, wherein the thermoplastic polymer is chosen from vinyl chloride resins, polyesters, polyurethanes, ethylene-vinyl acetate copolymer, rubbers, poly(meth)acrylics and combinations thereof.

10. The polymer composition of clause 9, wherein the thermoplastic polymer is polyvinylchloride.

11. A process for making compounds of the formula:

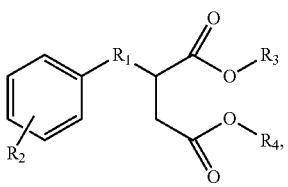

comprising reacting an aromatic compound of the formula:

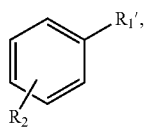

$R_1'$ represents $C_xH_{2x+1}$ wherein x=0-4 or cyclohexane; $R_2$ represents H, a $C_1$-$C_6$ alkyl group at any of the ortho-, meta- or para-positions, a residue including heteroatoms chosen from O, N, and S, or mixtures thereof; with maleic anhydride in the presence of a free radical alkylation initiator, to form compounds of the formula:

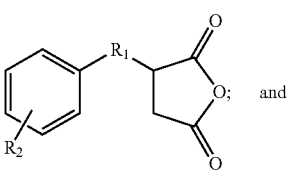

esterifying the anhydride moiety with one or more OXO-$C_5$-$C_9$ alcohols, which are different isomers of equal carbon number or different in carbon number under esterification conditions to form said compounds of formula:

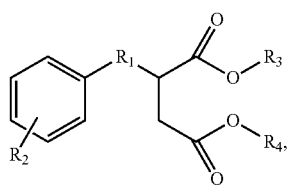

$R_1$ represents $C_xH_{2x}$ wherein x=0-4 or cyclohexane, and $R_3$ and $R_4$ represent hydrocarbon residues of said OXO-$C_5$-$C_9$ alcohols.

12. The process of clause 11, wherein $R_2$ is chosen from hydrogen, methyl, phenyl, and ethyl.

13. The process of clause 11 or 12, wherein the compounds formed are a mixture isomers, and wherein $R_2$ is in the ortho-, meta- and para-positions.

14. The process of clauses 11, 12 or 13, wherein $R_3$ and $R_4$ represent hydrocarbon residues of $C_6$ or $C_7$ OXO-alcohols.

15. The process of clauses 11, 12, 13, or 14 wherein the free radical initiator is chosen from air, n-hydroxyphthalimide (NHPI), azobisisobutyronitrile (AIBN), t-butylperoxide, cumene hydroperoxide, and combinations thereof.

16. A process for making compounds of the formula:

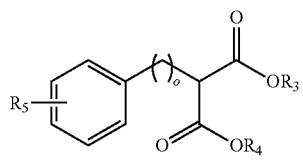

comprising reacting a compound of the formula:

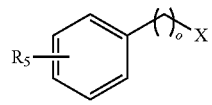

with a diester of malonic acid, wherein X is any halide, $R_5$ represents H, or $C_1$-$C_6$ alkyl at any of the ortho-, meta- or para-positions or mixtures thereof, $R_3$ and $R_4$ represent hydrocarbon residues of said OXO-$C_5$-$C_9$ alcohols, and o=0 or 1.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

What is claimed is:

1. A compound of the formula:

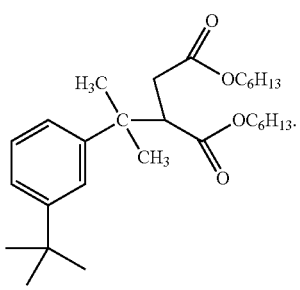

2. A polymer composition comprising a thermoplastic polymer and at least one plasticizer comprising a compound of the formula:

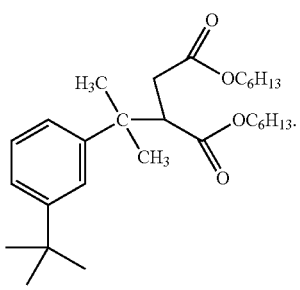

3. The polymer composition of claim 2, wherein the thermoplastic polymer is selected from the group consisting of vinyl chloride resins, polyesters, polyurethanes, ethylene-vinyl acetate copolymer, rubbers, poly(meth)acrylics and combinations thereof.

4. A process for making a compound of the formula:

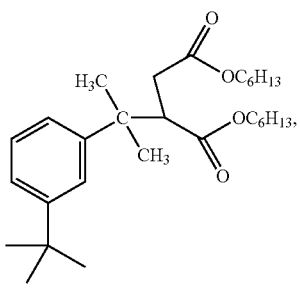

comprising:

reacting an aromatic compound of the formula

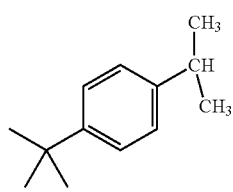

with maleic anhydride in the presence of a free radical alkylation initiator, to form a compound of the formula:

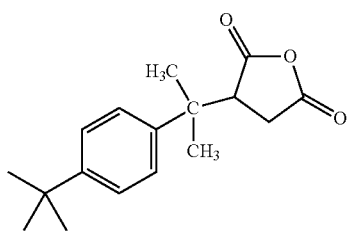 [SMILES: CC(C)(C)c1ccc(C(C)(C)C2CC(=O)OC2=O)cc1]

esterifying the anhydride moiety with one or more OXO-$C_6$ alcohols under esterification conditions to form said compound of formula:

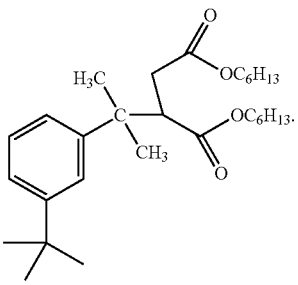

5. The process of claim 4, wherein the free radical initiator is air, n-hydroxyphthalimide (NHPI), azobisisobutyronitrile (AIBN), t-butylperoxide, or cumene hydroperoxide, or combinations thereof.

* * * * *